United States Patent [19]

Simons et al.

[11] Patent Number: 5,056,992

[45] Date of Patent: Oct. 15, 1991

[54] IV PUMP AND DISPOSABLE FLOW CHAMBER WITH FLOW CONTROL

[75] Inventors: Tad D. Simons, Menlo Park; Frederick A. Stawitcke, Sunnyvale, both of Calif.; William M. Reed, Carlisle; Paul A. Tessier, Hudson; Marc J. Zeitlin, Acton, all of Mass.

[73] Assignee: Hewlett-Packard Company, Palo Alto, Calif.

[21] Appl. No.: 314,322

[22] Filed: Feb. 22, 1989

Related U.S. Application Data

[60] Division of Ser. No. 56,189, May 29, 1987, abandoned, which is a continuation of Ser. No. 170,351, Mar. 16, 1988, abandoned.

[51] Int. Cl.⁵ .............................................. F04B 45/08
[52] U.S. Cl. ...................................... 417/474; 417/478; 417/479; 604/153
[58] Field of Search ....................... 417/478, 479, 474; 604/153, 250; 628/DIG. 12

[56] References Cited

U.S. PATENT DOCUMENTS

| | | | |
|---|---|---|---|
| 4,322,201 | 3/1982 | Archibald | 417/279 |
| 4,382,753 | 5/1983 | Archibald | 417/479 |
| 4,840,542 | 6/1989 | Abbott | 417/479 |
| 4,846,636 | 7/1989 | Danby | 417/479 |

Primary Examiner—Leonard E. Smith
Attorney, Agent, or Firm—Richard F. Schuette

[57] ABSTRACT

An apparatus and method are disclosed for an IV pump which can act also as a passive infusion controller. The apparatus has a disposable flow chamber with two pumping subchambers connected by a first collapsible passageway. A pump drive is used to operate the pumping subchambers and includes a first control valve for depressing the first collapsible passageway to control flow between the subchambers and an outlet control valve for depressing an outlet collapsible passageway to control flow of infusate out of the flow chamber. The flow chamber has a base surface and first and second caps, each cap being spaced apart from the base surface and having means for attachment to one of two moveable connector rods. The caps each act as one side of the first and second pumping subchambers, respectively, the base surface being the other side. A flexible wall is connected to the base surface and to each of the caps providing the subchamber volumes therebetween. The flexible wall is constructed of a material having a thickness and modulus of elasticity such that when the connector rods are not moving the flexible wall element does not collapse when subjected to a negative gauge pressure.

29 Claims, 35 Drawing Sheets

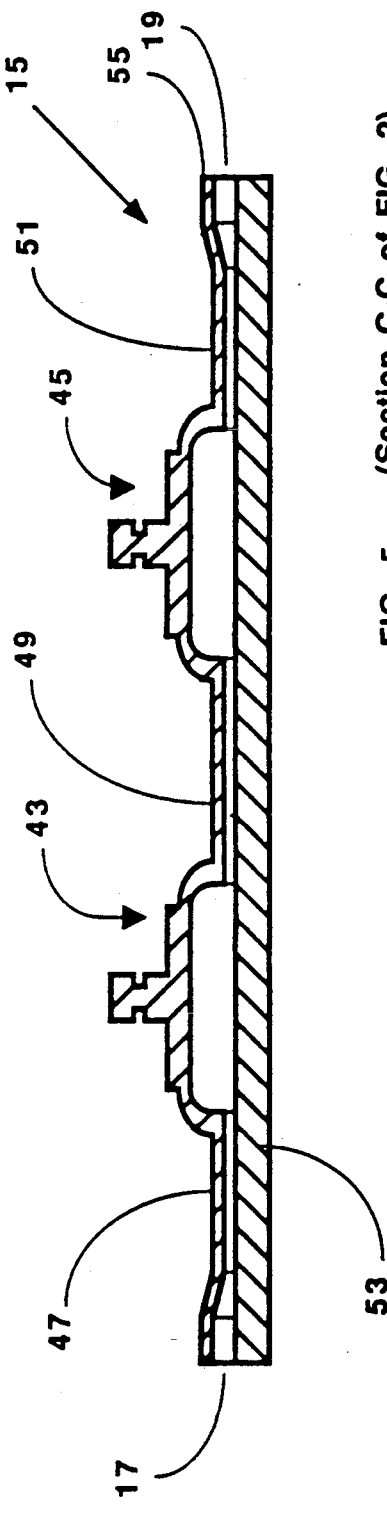
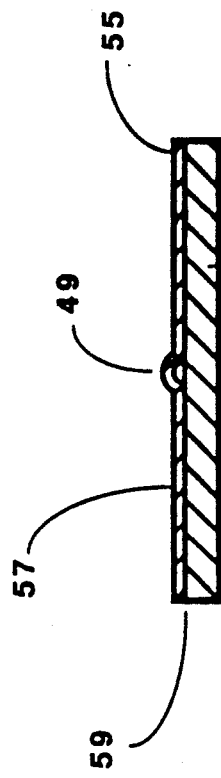
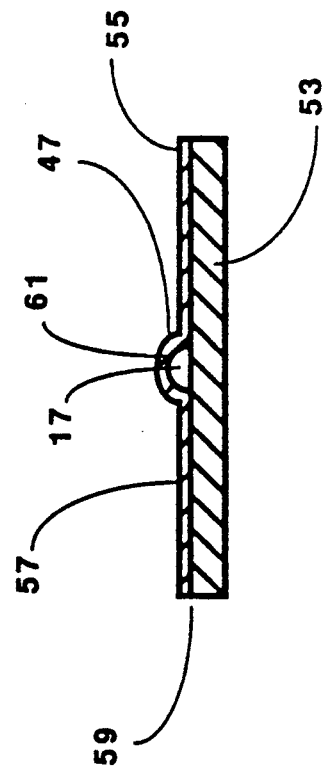

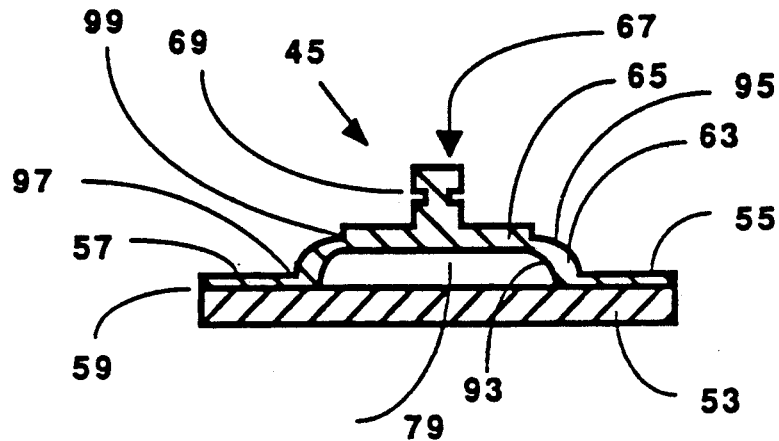
FIG. 6 (Section D-D of FIG. 2)
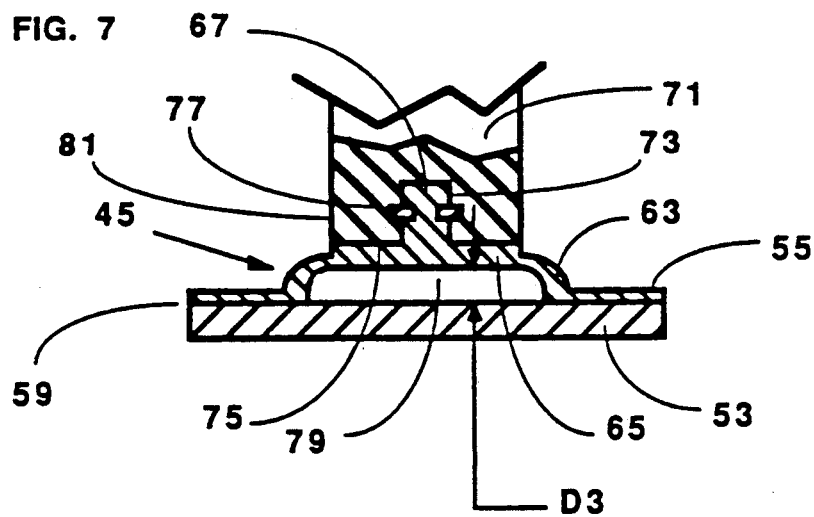
FIG. 7
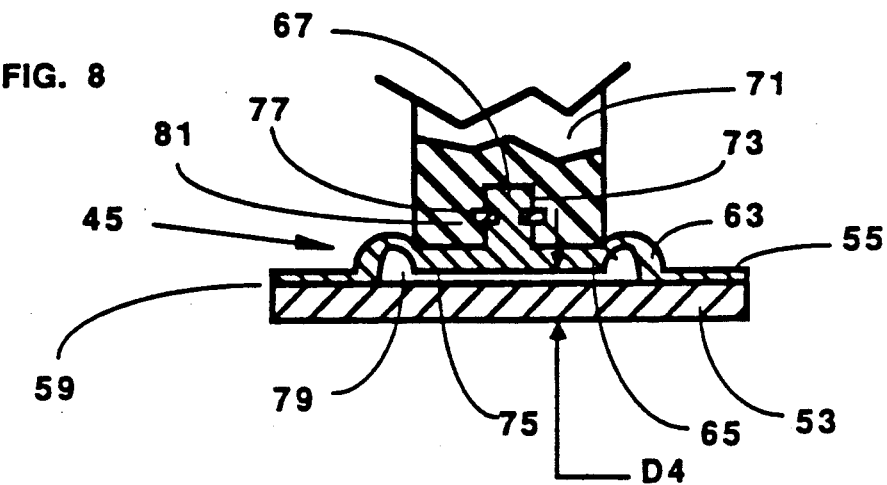
FIG. 8

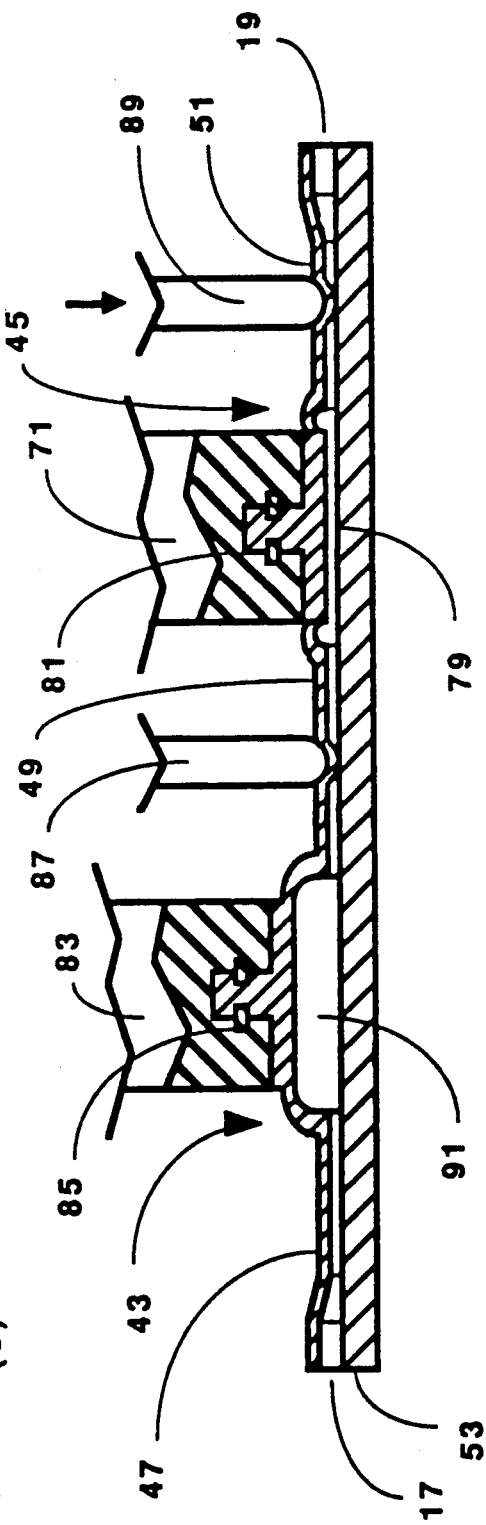

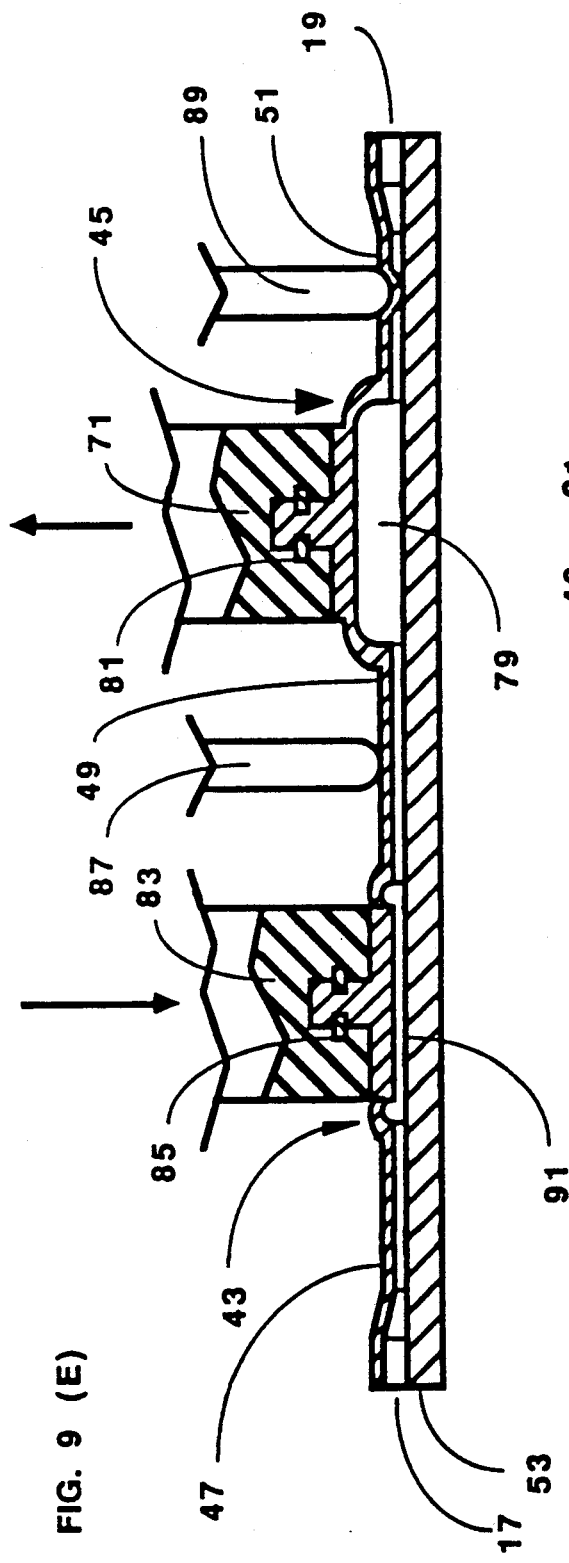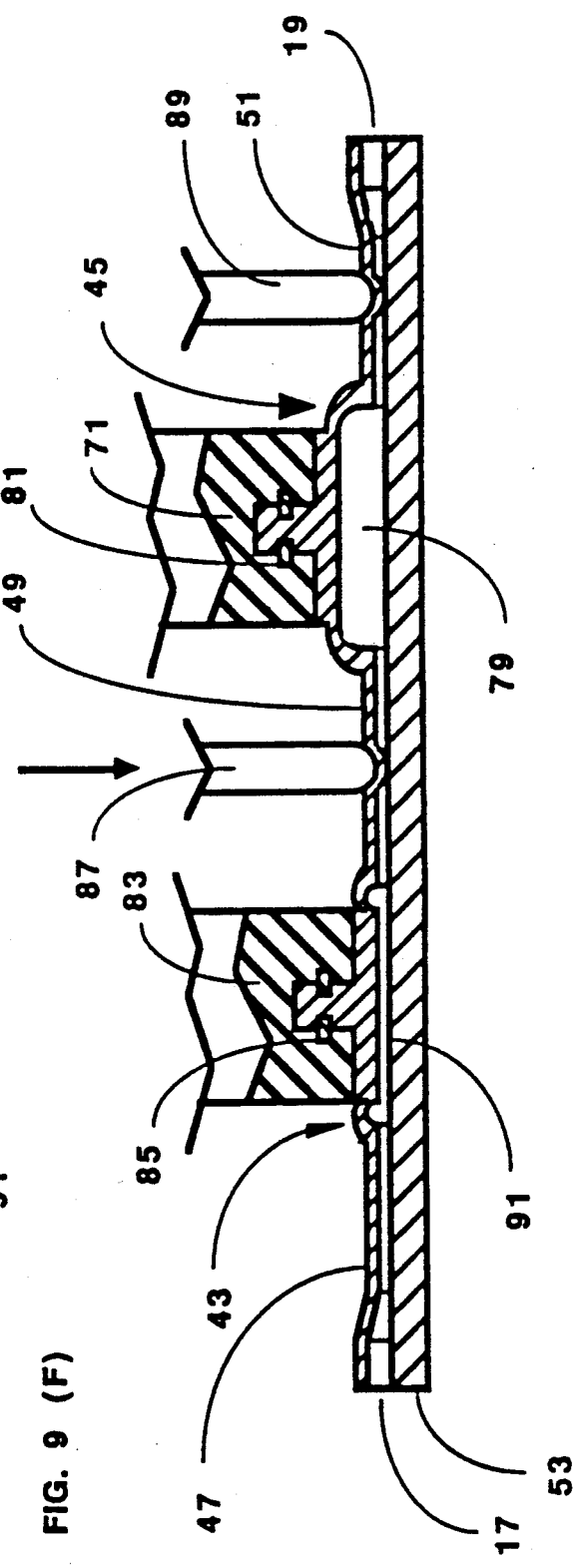

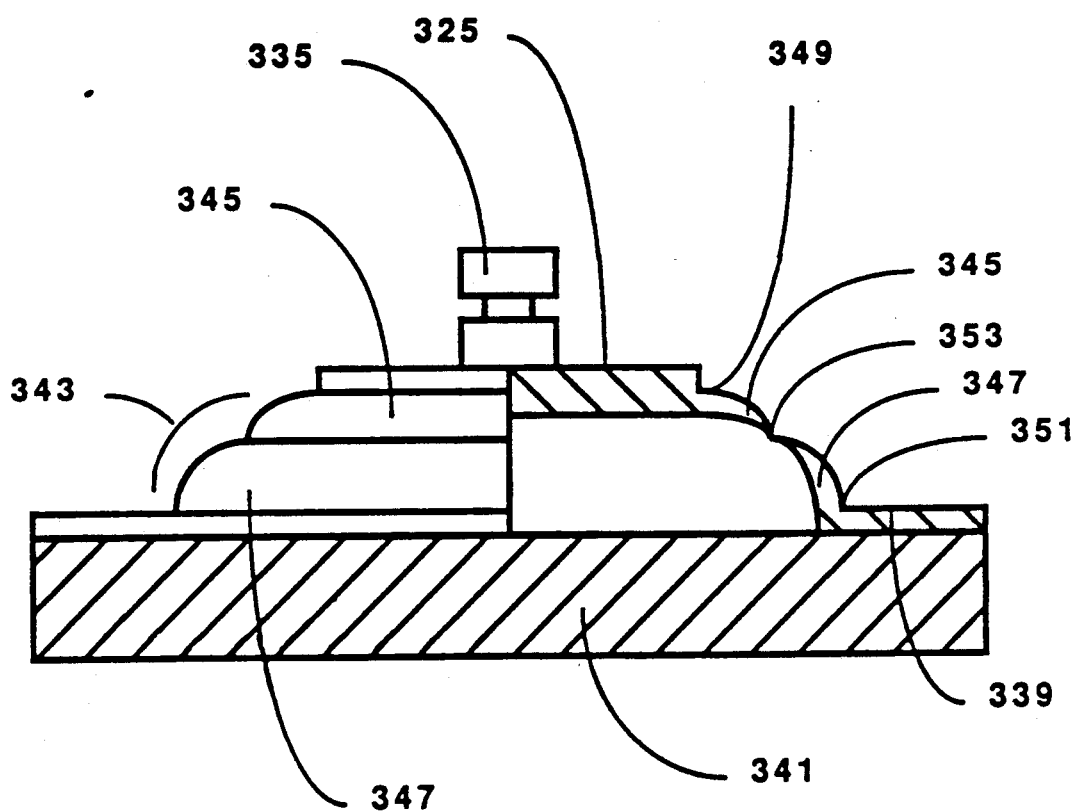

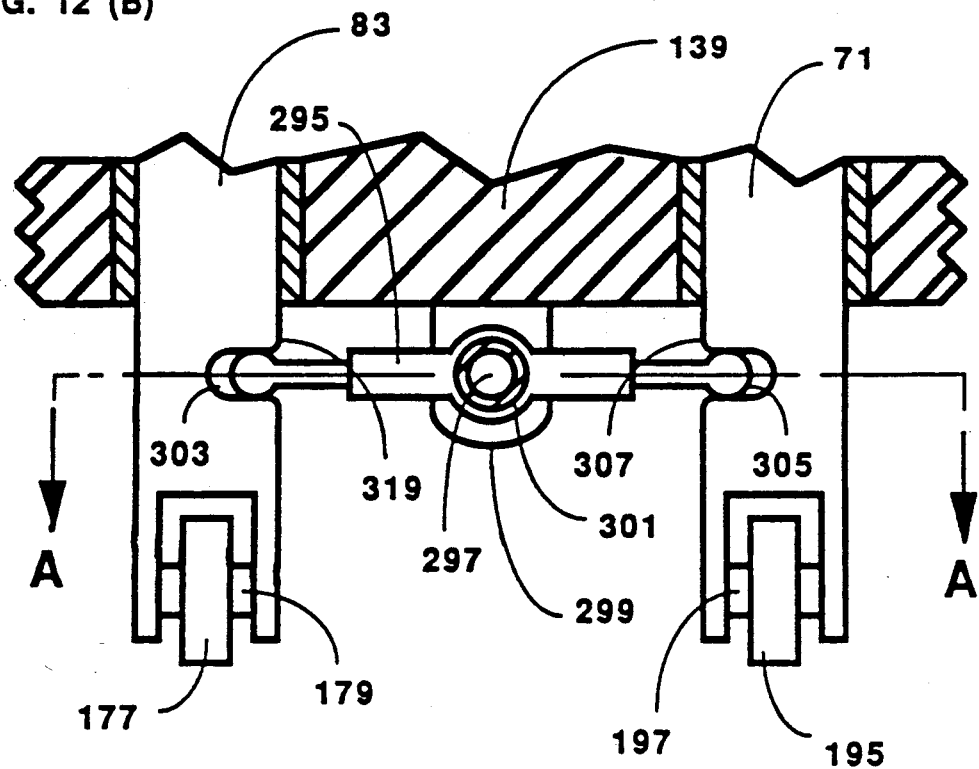
FIG. 12 (B)
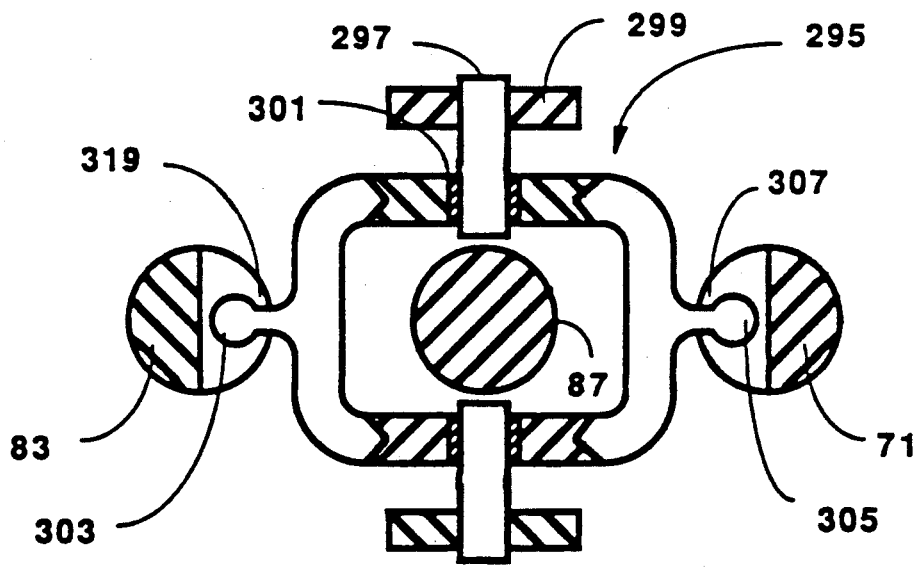
FIG. 12 (C) (Section A-A)

IV PUMP AND DISPOSABLE FLOW CHAMBER WITH FLOW CONTROL

This is a divisional of co-pending application Ser. No. 056,189 filed on May 29, 1987 which is a continuation-in-part of application Ser. No. 170,351, filed Mar. 16, 1988 both now abandoned.

BACKGROUND OF THE INVENTION

The present invention pertains to IV pumping apparatus, and particularly to volumetric pumps suitable also for controlling passive infusion and a method for achieving said control.

To improve health care, there has been considerable effort with regard to the administration of intravenous (IV) fluids. For many years IV solutions were administered only by the force of gravity. Generally, the volume rate was measured by counting the number of drops per minute. This method, however, has proved unsatisfactory for several reasons. For example, the drop size can vary considerably, since drop size is directly proportional to surface tension, which is affected by temperature and type of solution. Also the drop size is affected by the speed at which the drop forms. Further, the drop rate is affected by the restrictions of the tube and needle, and the drop-forming geometry. If a tube is partly occluded, the drop rate will decrease or as the IV supply decreases the hydrostatic pressure will decrease causing a decrease in drop rate. In many cases, therefore, the variability of both the drop size and the drop rate (both of which are for the most part beyond the control of the operator) makes this method of administration of intravenous fluid unsatisfactory.

Improvements have been made by adding an electronic drop counter together with either a controller or a peristaltic pump. The electronic drop counter and controller combination controls the drop rate, but makes no improvements in controlling drop size, and also has the deficiency of not being able to control drop rate if back pressure increases beyond the hydrostatic forcing pressure. The electronic drop counter and peristaltic pump combination increases the forcing pressure but lacks an accurate metering method.

Improvement in metering methods results with the use of displacement pumps, which offer the capability of greater precision in controlling IV flow rates than is possible with the prior art IV controllers which depend on gravity. These pumps, in addition to metering the fluid, also apply positive pressure to the fluid or the IV tubing. The displacement pump can generally be categorized as peristaltic (such as described in U.S. Pat. No. 3,737,251 by Berman et al) or piston-cylinder (such as described in U.S. Pat. No. 3,985,133 by Jenkins et al) or pulsating (such as described in U.S. Pat. No. 3,874,826 by Lundquist).

The peristaltic pump, although generally an improvement over the prior art, has a number of disadvantages. First, stretching an elastomeric material in a peristaltic manner does not lend itself to an efficient use of energy. Second, repeated stretching can irreversibly deform the material, causing changes in pump displacement, and possible failure. Further, because patients can be ambulatory and because of potential loss of power, a battery backup for the pump is required. Hence, it is desireable that the pump be as efficient as possible.

The piston-cylinder pumps of the prior art provide for accurate metering and positive pressure, but also have several disadvantages. First, because intravenous therapy requires that the pump maintain a sterile barrier, and cost prohibits cleaning and sterilization after each use, the pumping chamber must be disposable and inexpensive to manufacture. This has been difficult to achieve with the prior art piston-cylinder pumps. To reduce manufacturing costs, some prior art pumps use only one chamber and two valves. This requires that the pump cycle have two parts, a fill, and an empty; therefore, IV therapy is interrupted during the fill portion of the cycle. Second, the friction of a piston-cylinder pump is a cause for reduced efficiency.

The pulsating pumps provide a continuous pulsing flow, but also have significant disadvantages. First, the self-contained valving of these pumps has added to the complexity and expense of the disposable pump chamber. Second, the pulsating action against a spring load or an elastomeric material does not lend itself to efficient operation.

U.S. Pat. No. 3,809,507 by Baglai describes a pump which is not intended specifically for use in IV therapy, but which does provide a continuous pulse-free flow. The valves in this pump are either located on moving parts or located at a fixed location and connected by a flexible tube. This approach does not lend itself to an economical disposable pump chamber as is required for IV applications. Also, without the valves biased or powered, the pump in the off condition may continue to supply fluid (i.e. it suffers from "siphoning"). This is an unsafe condition for IV therapy.

Another pump design which is specifically adapted for infusing IV fluids is described in U.S. Pat. No. 4,410,322 by Archibald. That system also provides for a continuous flow and has a disposable pumping chamber. In that system, however, the individual pumping chambers are of a rolling diaphragm type design similar to the rolling diaphragm system described in U.S. Pat. No. 2,849,026 issued to Bellofram Corporation. A significant problem associated with such rolling diaphragm systems, however, is that the chamber wall has a tendency to collapse under negative gauge pressures, and renders the pumping chamber inoperative when pressure is restored. Hence, specific measures are taken to avoid negative pressure differentials across the diaphragm wall. Such negative pressures are often encountered in the patient care environment when a patient's infusion site is below the level of the pump.

What is needed is an energy efficient pump with an inexpensive disposable flow chamber that can deliver accurate volumes of infusate over a wide range of system pressures of clinical concern. Furthermore, it would be desirable if the pump itself could also be used as a flow controller in order that active pumping not be required continuously in order to deliver precise volumes of infusate and in order that the pump not be required to be removed for passive infusion.

SUMMARY OF THE INVENTION

In accordance with preferred embodiments of the invention an apparatus and method are disclosed for the pumping of IV fluids and for calibrating a passive infusion using the apparatus, i.e. the apparatus can act as an infusion controller when not being operated as an infusion pump. The apparatus is made up of a disposable flow chamber having first and second pumping subchambers connected by a first collapsible passageway, the flow chamber having an inlet passageway connected to the first subchamber for providing an infusate into the first subchamber. The flow chamber also has an outlet collapsible passageway connected to the second subchamber permitting infusate to exit from the second subchamber. A pump drive is used to operate the pumping subchambers. The pump drive includes a first actuator element for changing the volume of the first subchamber and a second actuator element for changing the volume of the second subchamber. The pump drive also includes a first control valve for depressing the first collapsible passageway to control flow between the first subchamber and the second subchamber, and an outlet control valve for depressing the outlet collapsible passageway to control flow of infusate leaving the second subchamber. The pump drive also has a motor for driving the first and second connector rod elements, the first control valve, and the outlet control valve in order to pump infusate through the flow chamber.

In a preferred mode a pivoted beam mechanism is used connecting the first actuator to the second actuator, so that as one subchamber is compressed the other is simultaneously restored to its original shape, thereby eliminating the need for return springs to hold the actuators to their respective driving elements of the motors.

The pump drive, with the same motor, can also move the outlet control valve while the first control valve is held fixed.

This latter feature of the pump drive is especially useful in carrying out the method of the invention for calibrating a passive infusion system to deliver a prescribed flow rate, i.e. when acting as an infusion controller. According to the method, a drip chamber is connected to a volumetrically controlled pump, for example, such as the apparatus of the invention. The volumetric pump is operated at a rate to achieve the given flow rate. The number of drops per unit time is counted during pumping to arrive at a drip rate corresponding to the given flow rate. Then the pumping is stopped and the drip rate is adjusted to achieve the desired flow of infusate. In this latter step, using the apparatus of the invention, the pump remains in line with the first control valve open, and the outlet control valve is adjusted to achieve the drip rate which was determined during the pumping step. Appropriate interrupts can then be used throughout the passive infusion to recalibrate and thereby ensure an accurate infusion rate.

A significant aspect of the invention is the disposable flow chamber itself. The flow chamber has a base element for providing a base surface which in the preferred mode, is made of a material that is smooth, stiff, and non-compliant under the pumping pressure. The flow chamber has a first top portion with an inner surface spaced apart from the base surface and an outer surface having means for contacting one of the two movable actuators. The first top portion is constructed of a material that is dimensionally stable and retains its shape under the pumping pressure when contacting an actuator. This first top portion acts as one side of the first pumping subchamber, the base surface being the other side. The rest of the first pumping subchamber is defined by a first flexible wall element connected to the base surface and to the inner surface of the first top portion providing a volume therebetween. The flexible wall element is constructed of a material having a thickness and modulus of elasticity such that when the actuator is not moving the first top portion, the first flexible wall element does not change shape when subjected to a negative gauge pressure, i.e. it does not collapse or buckle inward. However, the elasticity and thickness of the flexible wall element is also such that the first flexible wall element bends when the top portion moves the first cap element relative to the base surface.

The second pumping subchamber has similar characteristics to the first pumping subchamber, and in the preferred mode is identical in shape, volume, and construction.

In some preferred embodiments, the drive system uses connecting rods as the actuators which connect to the pumping subchambers and operate them. In other embodiments, the actuators do not actually connect to the pumping subchambers but merely contact them, relying on the restoring force of the flexible sidewalls to restore the shape of the subchambers when not being compressed by the actuators. In these latter embodiments, the pumping subchambers have a domed top portion for contacting the actuators, and the actuators are conformed to the shape of the top portion so that no substantial distortion of the top portion can take place during pumping. This ensures dimensional stability and a repeatable volume of flow for each pumping cycle. In these latter embodiments, as in the previous embodiments, the flexible walls bend under the action of the actuators in the process of driving the pumping subchambers.

The present invention operated as a volumetric pump has many advantages. The subchambers of the disposable flow chamber are of a unique design, providing an effective compromise between stiffness and compliance, so that pumping is accomplished with a minimum energy input while the pliant structures remain substantially insensitive to positive or negative pressure fluctuations. The system is not volume compliant, a decided advantage for accurate delivery of precise amounts of infusate. The operation as a pump and as a controller using a single drive, incorporating a valve used in the pump mode as a control valve in the controller mode reduces the complexity of the flow control mechanism. The pivoted beam arrangement together with the unique subchamber design provides a particularly energy efficient design.

BRIEF DESCRIPTION OF THE DRAWINGS

FIG. 3 is a longitudinal section view of the disposable flow chamber of FIG. 2.

FIG. 4 is a lateral section through a collapsible passageway of the disposable flow chamber of FIG. 2.

FIG. 5 is a lateral section through a second collapsible passageway of the disposable flow chamber.

FIG. 6 is a lateral section through the disposable flow chamber bisecting a pumping subchamber.

FIG. 7 shows the section of FIG. 6 with a connecting rod attached to the pumping subchamber.

FIG. 8 illustrates the action of the connecting rod of FIG. 7 to cause pumping.

FIG. 9 (B) illustrates a first action in a pumping cycle for the arrangement of FIG. 9 (A).

FIG. 9 (C) shows a second action of a six phase pumping cycle.

FIG. 9 (D) illustrates a third action of the pumping cycle.

FIG. 9 (E) shows a fourth action of the pumping cycle.

FIG. 9 (F) shows a fifth action of the pumping cycle.

FIG. 9 (G) shows a final sixth action of the pumping cycle.

FIG. 10 (B) shows another alternative embodiment of a subchamber for the disposable flow chamber.

FIG. 10 (C) is a top plan view of yet another alternative embodiment of a subchamber for the disposable flow chamber.

FIG. 10 (D) is a section view of the subchamber of FIG. 10 (C).

FIG. 10 (E) is another section view of the subchamber of FIG. 10 (C).

FIG. 10 (F) is a plan view of yet another alternative embodiment of a subchamber for the disposable flow chamber.

FIG. 10 (G) is a section view of the embodiment shown in FIG. 10 (F).

FIG. 10 (H) is a plan view of yet another alternative embodiment of a subchamber for the disposable flow chamber.

FIG. 10 (I) is a section view of the embodiment shown in FIG. 10 (H).

FIG. 12 (B) is a face-on view of part of the section of FIG. 12 (A) showing a hinged beam for use in a preferred embodiment with the flow control mechanism.

FIG. 12 (C) also shows the hinged beam of FIG. 12 (B).

FIG. 17 (B) is a cam profile for a transfer valve cam.

FIG. 17 (C) is a cam profile for a pump cam.

FIG. 17 (D) is a cam profile for an exit valve cam.

FIG. 17 (E) is a cam profile for a servo cam.

DESCRIPTION OF THE PREFERRED EMBODIMENTS

Figure 1:
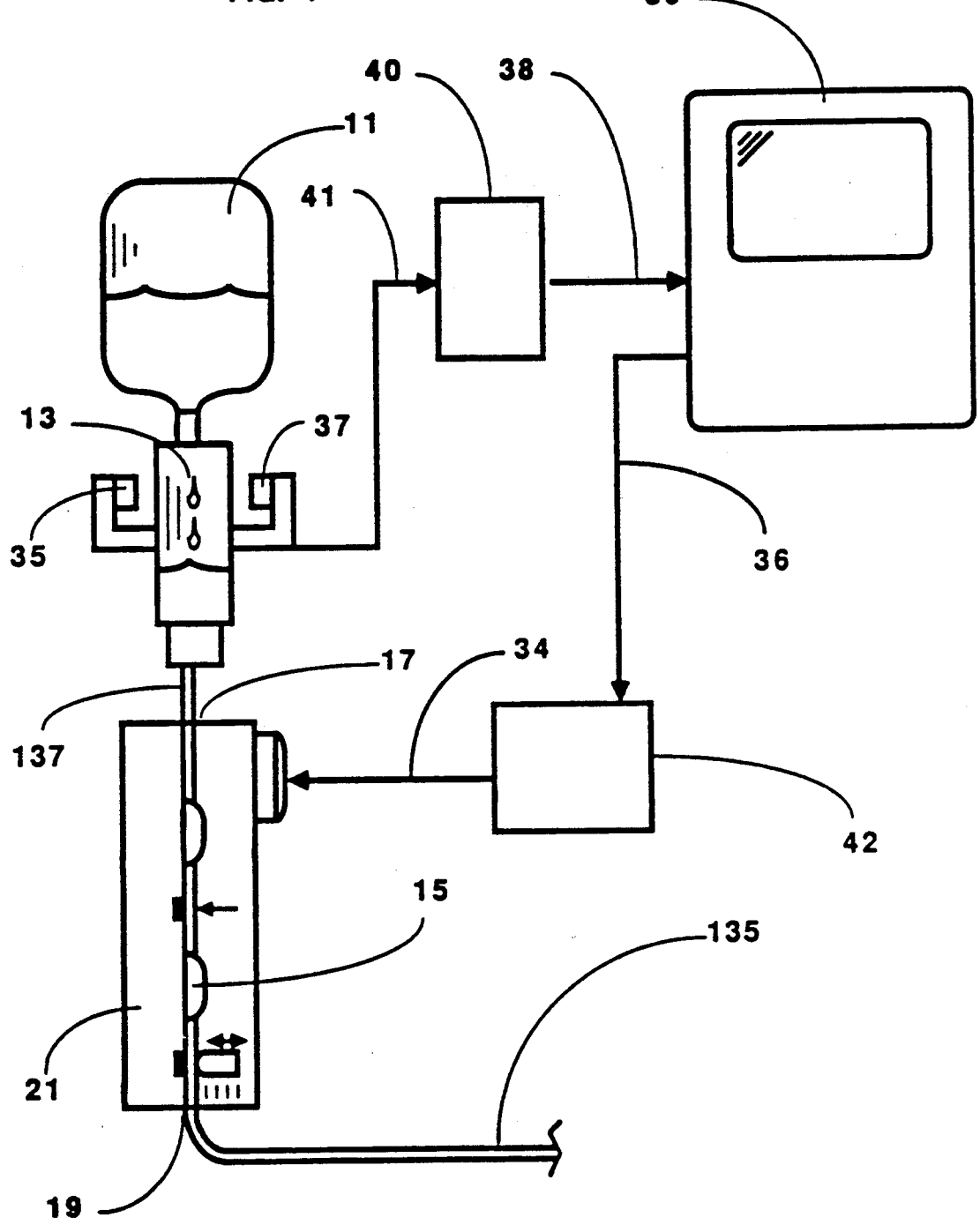
FIG. 1 is a schematic representation of an IV pump system according to the invention.

FIG. 1 is a schematic diagram showing principal parts of a preferred embodiment of the present invention. The diagram of FIG. 1 shows an infusion pump system as used in the medical arts for infusing fluids into the veins, arteries of patients, or organs. The system includes an infusate reservoir 11 of a conventional kind connected to a transparent drip chamber 13, which is connected by flexible rubber or elastomeric tubing 137 to an inlet end 17 of a disposable flow chamber 15. The disposable flow chamber is a sterile, versatile unit used for pumping and flow control of infusate, and is caused to act by an electrically powered flow control mechanism 21, into which a new disposable flow chamber may be assembled for each new infusion process. Disposable flow chamber 15, under the influence of flow control mechanism 21 can operate in either of two modes: as a precise volumetric pump, drawing fluid through drip chamber 13 and supplying same to a patient; and as a drip rate servo controller, controlling the opening of a servo valve in response to sensed, programmed or manually input information, to control flow by drip rate, with impetus to flow provided by the gravimetric pressure head of an elevated infusate reservoir above the controller and the patient.

An optical light source 35 is sighted through transparent drip chamber 13 to optical light sensor 37, providing a light beam to be altered each time a drop passes through the light beam. Alteration of the light beam produces a momentary change in the electrical signal which is communicated via optical sensor and power signal line 41 to a sensor interface 40 where the signal is conditioned to a type acceptable to a digital controller, and isolated from outside noise. The conditioned signal is communicated via line 38 to a central processing unit (CPU) 39, which is a digital processor and controller.

CPU 39 may accept manually input signals or may operate by a previously programmed algorithm. The CPU, in a preferred embodiment, monitors signals from the optical sensors at the drip counter, records the time interval between signals, and calculates and records information about the drip rate.

CPU 39 through a communication link 36 operates a motor interface 42 where digital signals are reconditioned to operate motor drive circuits in a manner to drive an electric motor through a power control cable 34. The motor provides the motive power for flow control mechanism 21. In a preferred embodiment, rotation of the motor in one direction will cause operation as a precise volumetric pump. The drive may be stopped and rotation reversed for a part of a revolution, during which a servo valve is opened in disposable flow chamber 15 by an amount monotonically increasing with the degree of reverse revolution. In a preferred embodiment, operating with a programmed input, CPU 39 will vary the opening of a servo valve in response to information previously stored about drip rate, maintaining a drip rate established during operation as a volumetric pump.

DISPOSABLE FLOW CHAMBER

Figure 2:
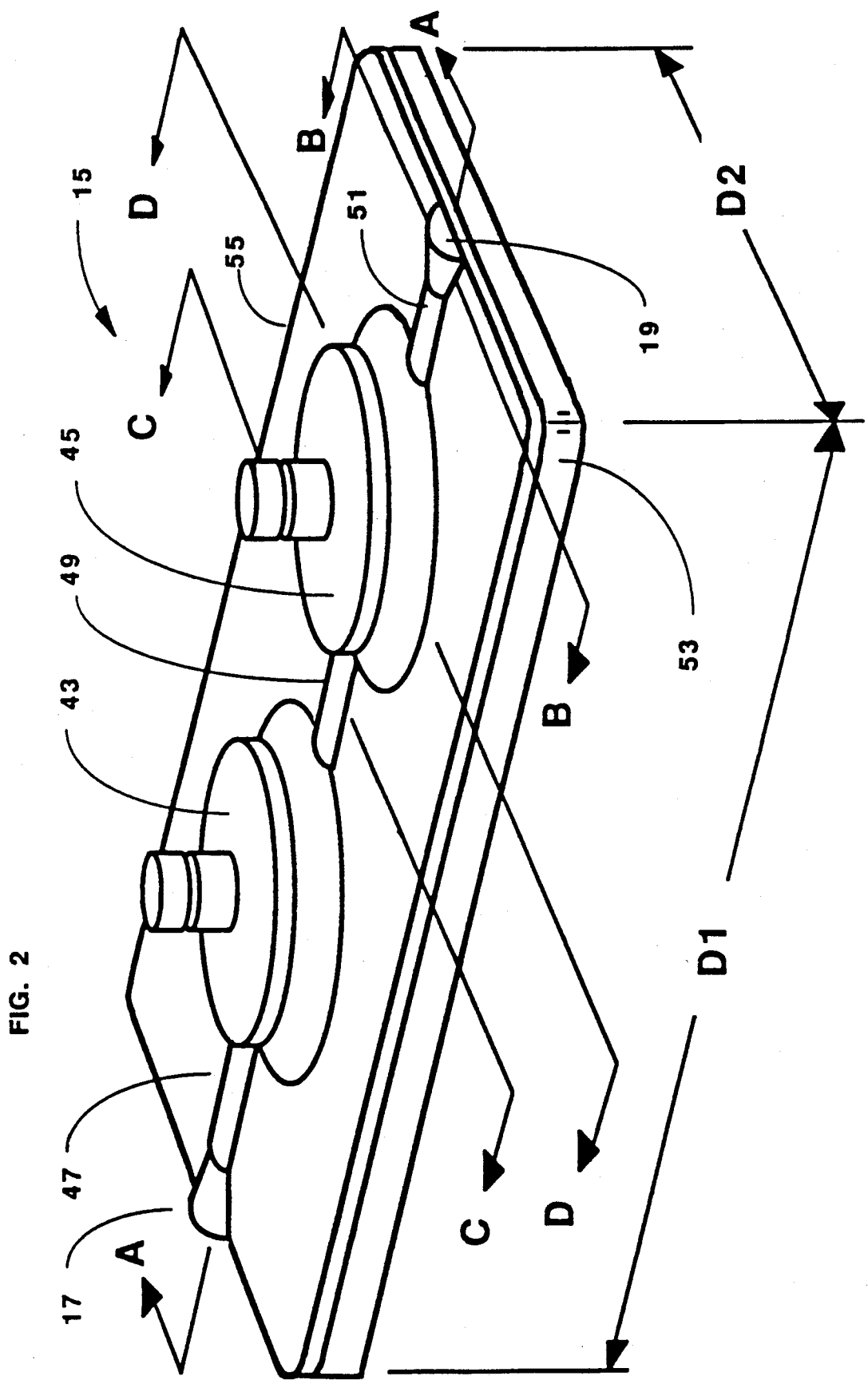
FIG. 2 is a perspective view of a disposable flow chamber as used in a preferred embodiment of the invention.
Figure 9:
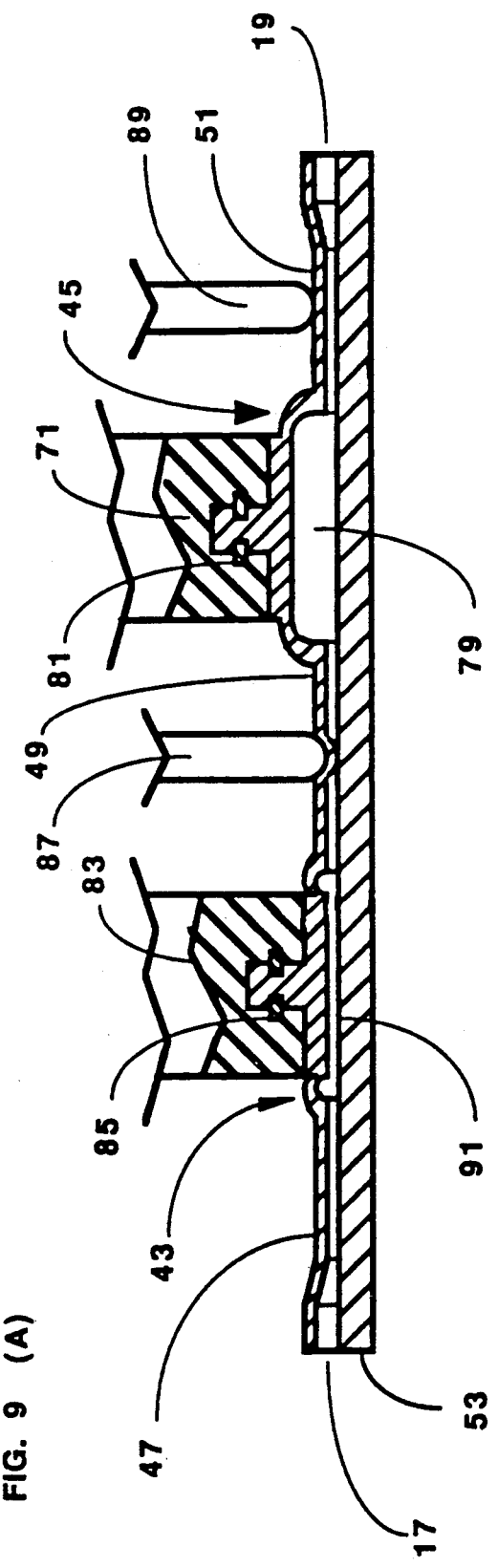
FIG. 9 (A) is a longitudinal section of the disposable flow chamber showing connecting rods attached to the two subchambers and two valves positioned at two collapsible passageways. The parts are shown in a "home" position.
Figure 9:
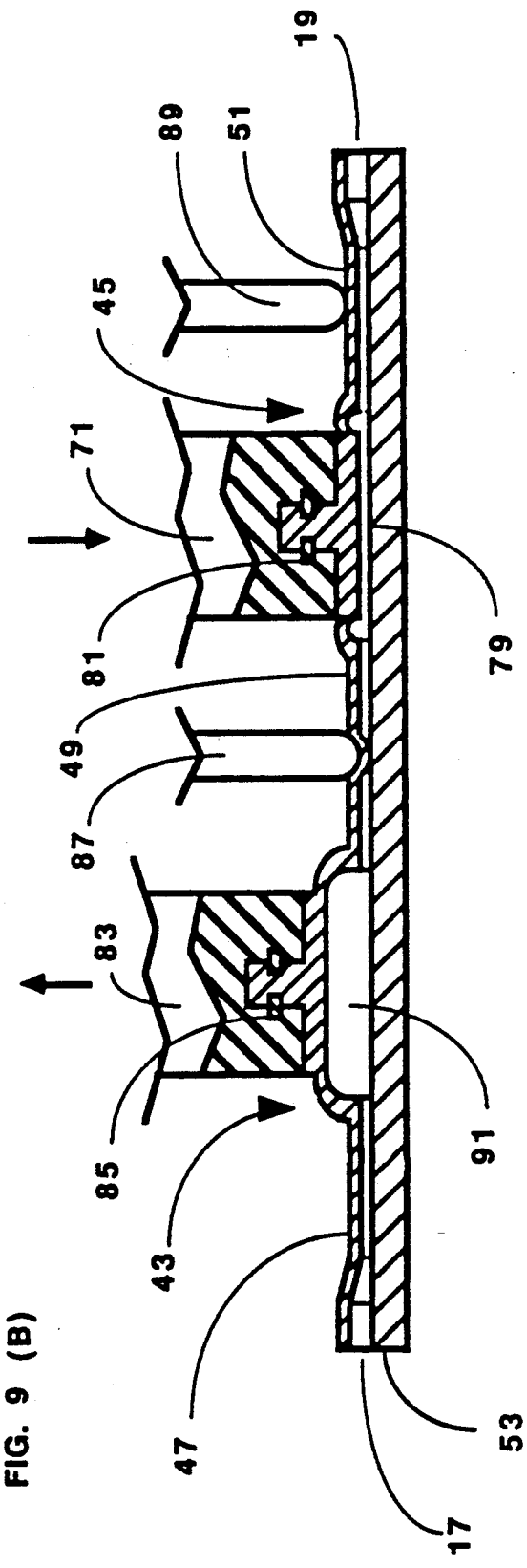
Figure 9:
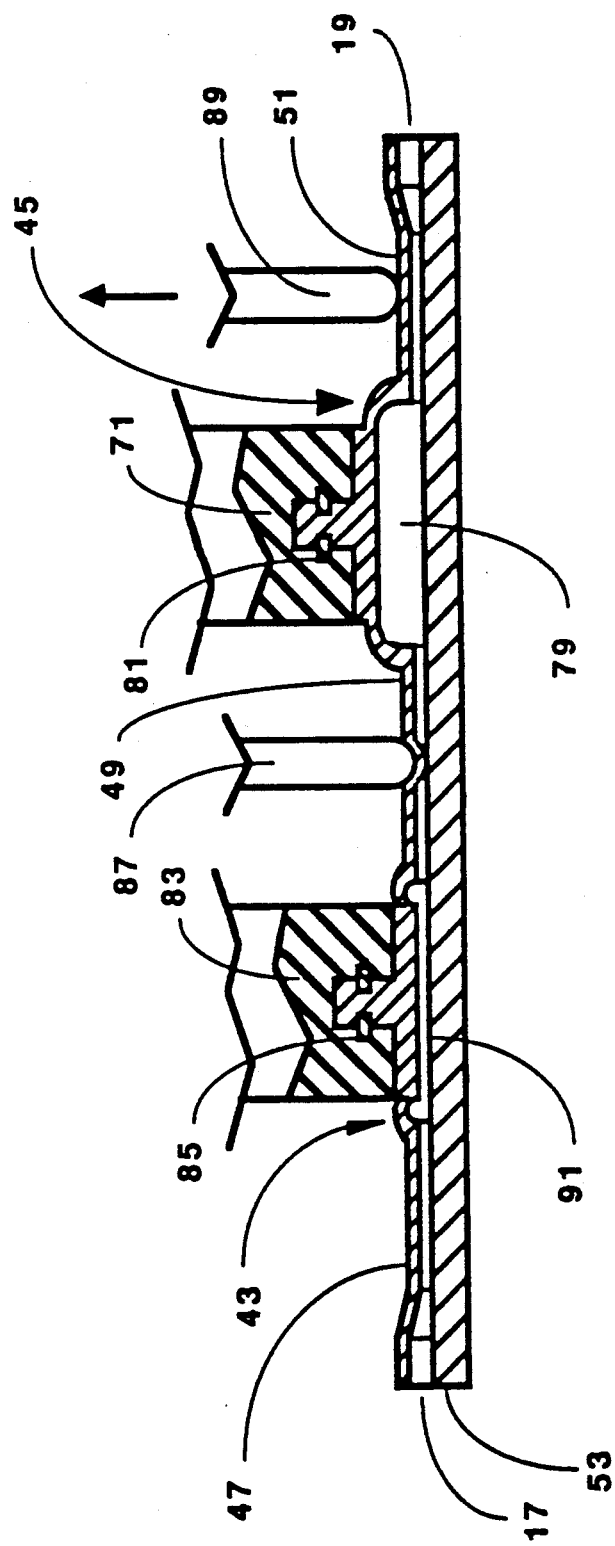

FIG. 2 is a perspective view of a preferred embodiment of a disposable flow chamber 15. The orientation of the flow chamber during use is as illustrated in FIG. 1. However, for purposes of illustration of the details of the flow chamber, the horizontal orientation shown in FIG. 2 will be used. The flow chamber includes two subchambers of precise and equal volume, a fill subchamber 43 and a pump subchamber 45. Subchambers 43 and 45 are connected in series by thin collapsible passageways that lead from one end of the disposable flow chamber to the other end. A passageway 47 begins at inlet end 17 and leads to fill subchamber 43, the passageway 47 acting as a passive valve. A collapsible passageway 49 connects fill subchamber 43 to pump subchamber 45, and acts as a binary valve. A collapsible passageway 51 leads from pump subchamber 45 to outlet end 19, and acts as a binary valve and as an adjustable valve.

The valving function for these collapsible passageways occurs in conjunction with a drive system, which will be discussed subsequently, that depresses the passageways to restrict the flow therethrough. In this preferred embodiment, this valving function depends on the elasticity of the passageways to bring the passageways back to their normal open positions when they are no longer depressed, although the fluid pressure could also be used as the primary restoring force to restore the passageways to their open (home) position if it would be acceptable to have a valve which collapsed when the fluid pressure were low.

In this preferred embodiment, length D1 of flow chamber 15 is typically about 11.5 cm. and width D2 is about 5 cm. Subchambers 43 and 45 are objects of revolution approximately 2.5 cm.in diameter, and are spaced apart, center-to-center, about 4 cm. The line of subchambers 43 and 45, along with passageways 47, 49 and 51, is spaced centrally on the width D2. Furthermore, although flow chamber 15 is shown to be symmetric, relative to a plane drawn through the center of subchambers 43 and 45, and perpendicular to the base plane of the flow chamber, that symmetry is not required. These dimensions and placements are definitive for this preferred embodiment only, and may vary considerably for other embodiments of the invention. With these preferred dimensions, the volume associated with subchamber 43 or 45 is typically about 1 ml.

FIG. 3 is a sectioned view of disposable flow chamber 15 taken along central line A—A of FIG. 2. FIG. 4 is a lateral section across the flow chamber near inlet end 17 along line B—B, showing inlet end 17 having an arched shape. FIG. 5 is a lateral section at line C—C, showing flow passageway 49 as arched in shape, which is also typical of all connecting passageways, although other shapes which can be suitably collapsed to perform the valving functions can be used. Furthermore, the wall thickness can be varied from one collapsible passageway to another and the particular shapes of the passageways need not be the same. FIG. 6 is a section through pump subchamber 45 along line D—D, also typical of identical fill subchamber 43.

FIG. 3 illustrates the construction of the flow chamber 15 in two portions, a base portion 53 and a molded portion 55. Molded portion 55 is formed from a medically compatible flexible elastomer, such as silicone rubber or PVC, and the material used is preferably transparent, so that infusate flow and such things as bubble formation may be monitored visually during operation.

Base portion 53 is a flat piece of a transparent material, having a length and width equal to dimensions D1 and D2, respectively, of FIG. 2. The base portion forms the base, or foundation, of the disposable flow chamber, and has a thickness chosen so that this base is relatively stiff and does not flex appreciably during pumping or filling of the subchambers, so that the system remains dimensionally stable in order to provide adequate control of the pumped volume. In this preferred mode, using PVC for base portion 53, a typical thickness is 1.25 mm to 2.5 mm, although other thickness can be used depending on the desired stiffness. Also, other materials may require different thicknesses as well.

Molded portion 55 includes shapes, depressions, wall thicknesses and projections so that when the molded portion is joined to base portion 55, the subchambers and passageways afore-described are formed. Much of molded portion 55 is a flat sheet similar to base portion 53, but of lesser thickness. Portion 57 shown in FIG. 4,5, and 6 is typical. The thickness of flat portion 57 of molded portion 55 is typically 0.25 to 0.75 mm., although these limits may be exceeded in other embodiments.

Section view FIG. 4 shows how the shape of molded portion 53 describes an arch so that passageway 47 is formed when base portion 55 and molded portion 53 are brought together at line 59, the flat surfaces of molded portion 53 being brought into juxtaposition to the upper surface of base portion 55 which is also flat. In forming the passageway 47, the wall thickness over arched portion 61 in this preferred embodiment is shown the same as for flat portion 57. However, in some applications a different thickness may be desired for the wall as compared with the flat portion. Near inlet 17, as shown in FIG. 4, the height of the arch forming passageway 47 is typically 0.25 cm. and the width twice that dimension, or about 0.5 cm., in order to attach the flow chamber to appropriate tubing. These dimensions may vary in other embodiments.

Section view FIG. 5 shows how the shape of molded portion 53 describes an arch so that passageway 49 is formed when base portion 55 and molded portion 53 are brought together at line 59, flat surface to flat surface. The wall thickness for passageway 49 in FIG. 5 is the the same as the thickness for the flat, just as for passageway 47 of FIG. 4. The height of passageway 49 is typically 0.75 mm. to 1.25 mm. and the width is approximately twice that, or 1.5 mm. to 2.5 mm. although these limits may vary depending on the particular embodiment. The above dimensions for the preferred embodiment are typical for passageways 47, 49, and 51 at all positions except near the ends at inlet end 17 and outlet end 19, where the passageway size is increased, as shown in FIG. 4. Also, as indicated earlier, the different passageways may have different shapes and different cross-sectional areas. The increase at inlet and outlet is to facilitate the joining of tubing to flow chamber 15 for transport of infusate to and away from the flow chamber. In some embodiments there need not be a change in passageway size, and in some situations it may be desirable to provide a rounded portion on base 55 opposite the arched passageways to better accommodate attachment to tubing.

The joining of base half 53 to molded half 55, which joining forms the aforesaid passageways and chambers, may be accomplished by any of several methods. For certain materials, such as PVC, there are suitable adhesives that are reliable and medically compatible. Hence in the preferred mode, the joining is accomplished by adhesive bonding. In other embodiments other materials or other methods may be preferred. For instance, in an embodiment in which polyurethane is the material of construction, it would be convenient to heat seal base half 53 to molded half 55, because polyurethane is a material with a relatively low melting point for which heat sealing works reliably. The use of adhesives and solvents can thus be avoided. Similarly, the method of molding is considered to be a choice of application, convenience and cost under varying conditions. Some materials may be vacuum formed, some compression molded with heat, some injection molded, and some blow molded, among other methods. The method of the preferred embodiment described herein is injection molding. There may also be applications in which a one piece molding technique would be preferred, and two piece joining would not be required.

FIG. 6 shows a section through the center of pump subchamber 45. This section is typical also of fill subchamber 43. The chamber formed between base 53 and molded portion 55 includes an arched sidewall 63, a flat top portion 65 oppositely disposed to base 53, and a connector nib 67 which has a retainer groove 69. Clearly other retaining means can also be used. For example, a slide-in wedge shape on the cap with a mating part on the drive could be used to securely and accurately attach the cap to the drive. The purpose of fill and pump subchambers 43 and 45 is the movement of fluid infusate in a precise volumetric manner. FIG. 7 shows the cross-section of FIG. 6 also including a connector rod 71 shown in partial section, which has a center hole 73 into which connector nib 67 projects, a flat end 75 which in this preferred embodiment is shown as the same diameter as subchamber top 65 and fits flush to the top 65 when joined over nib 67. A groove 81 for retaining ring 77 which expands also into groove 69 of nib 67 when connecting rod 71 is joined to top 65 of subchamber 45. The purpose of connecting rod 71 is to move the top of subchamber 45 relative to base 53 so volume 79 inside the subchamber may be varied to cause a pumping action. Clearly, the diameter of the connecting rod need not be the same as flat portion 65 if flat portion 65 is provided with a suitable stiffness.

In FIG. 8, connecting rod 71 has been moved relative to flow chamber 15 while base 53 of flow chamber 15 was held fixed, resulting in top 65 of subchamber 45 moving close to base 53. The height of subchamber volume 79 before such pump stroke is typically 2.25 mm. The length of stroke of connector rod 71 from the position of FIG. 7 to the position of FIG. 8 is typically 2 mm., so, at the end of such stroke, the remaining clearance between base 53 and subchamber top 65 is 0.25 mm. shown as D4 in FIG. 8. Volume 79 is reduced a precise amount by the pumping stroke. The volume reduction is approximately the diameter of top 65 times the connector rod stroke. In this embodiment the diameter of top 65 is about 2.5 cm. and the stroke is about 2 mm., so the swept volume is about 0.75 ml. It should be understood that the stroke of 2 mm. was chosen for convenience and to obtain a 0.75 ml volume sweep. As a practical matter, the stroke could be suitably increased to nearly 2.25 mm. Given the materials used for constructing the flow chamber, however, it is preferred that the stroke length be chosen so that the inside of top 65 does not actually contact base 53, to avoid jamming the mechanism.

The operation of disposable flow chamber 15 as a volumetric pump is illustrated by FIGS. 9A–9G, which show a lengthwise section of flow chamber 15 at different phases during operation. Connector rods 71 and 83 are attached to pump and fill subchambers 45 and 43 by retainer rings 81 and 85 respectively, and connector rod 71 is shown attached to subchamber 45 as in FIG. 8. The pumping mechanism also includes two valve closure rods 87 and 89, with closure rod 87 operable at collapsible passageway 49 and closure rod 89 operable at passageway 51. The closure rods perform valve actions. When a closure rod is pressed against a thin collapsible passageway, the passageway is collapsed and compressed so that infusate may not pass through the position where the pressure is applied. Pumping operation is accomplished by a flow control mechanism not shown in FIGS. 9A–9G, which will subsequently be fully explained.

In the preferred embodiment, the flow control mechanism moves the rods in a fashion that causes pumping through disposable flow-chamber 15 in a six phase cycle. FIG. 9A shows a starting position in which connecting rod 83 has been moved toward base 53 reducing volume 91 to a minimum amount, valve closure rod 87 has been moved toward base 53 to a position at which collapsible passageway 49 has been completely closed, connecting rod 71 is withdrawn to a position where volume 79 of pump chamber 45 is maximum, and valve closure rod 89 is withdrawn so passageway 51 is adequately open. Those skilled in the art will understand that passageway 51 need not be completely open, but can be slightly depressed by valve rod 89, as long as adequate volume can flow therethrough. Generally, it is preferred that even in the open position that the valve rod touch the passageway to minimize the stroke length required. Also, the valve can then operate in a graduated manner, so that each motion of the rod directly affects the cross-sectional area of the passageway. In a first pumping and filling phase, connector rod 71 moves forward forcing displaced fluid through collapsible passageway 51, out of outlet end 19 to the patient. The volume pumped is a precise amount tested by empirical measure, and repeatable. At the same time connector rod 83 retracts, increasing the volume 91 of fill subchamber 43 by exactly the amount of infusate forced out of pump 45. Infusate is drawn in from an attached reservoir through tubing attached at inlet end 17. This action is shown by the new positions of the components in FIG. 9B. The second phase is the closure of passageway 51 at exit end 19 by movement of valve closure rod 89, shown complete in FIG. 9C. The third phase is the opening of passageway 49 by retraction of valve closure rod 87, shown complete in FIG. 9D. The fourth phase is a transfer phase in which connector rod 83 advances and connector rod 71 retracts, moving a volume of infusate from fill subchamber 43 through passageway 49 into pump subchamber 45, and the volume transferred is the precise volume pumped in the aforementioned pump phase. The completion of phase 4 is shown by FIG. 9E. The fifth phase closes passageway 49 by movement of valve closure rod 87, shown complete in FIG. 9F. The sixth and last phase of the cycle illustrated in FIG. 9G is retraction of valve closure rod 89 opening passageway 51 at the exit end 19, and the cycle is complete and can begin again.

Further details of the pump subchambers will now be described. The design of the identical fill and pump subchambers 43 and 45 for flow chamber 15 in the preferred embodiment is a result of careful calculation and testing, resulting in significant advantages over the prior art. Unlike chambers of the prior art, such as flexible rolling diaphragm chambers, the pump and fill chambers of the disposable flow chamber of the present invention are self-supporting, and offer a substantial resistance to changes in volume due to overpressure and do not collapse under negative gauge pressure. As discussed earlier, base 53 is of considerable thickness, usually more than 1.25 mm. and up to 2.5 mm., and does not flex in operation. Base 53 is also maintained on a rigid support in flow control mechanism 21, to be subsequently described. Top portion 65 is also of considerable thickness, typically about 0.5 mm., and is supported against the flat end of connector rod 71 as shown in FIG. 7, and is held thereto by retaining ring 81. Flat portion 57 of molded portion 55 is held firmly to supported base 53 by adhesive or heat seal joining as described earlier. Only the short arched sidewall 63 of the subchamber deforms when a pump or fill stroke is performed.

As viewed in cross-section, in FIG. 6 the arched sidewall 63 in the preferred embodiment is composed of an approximately circular arch made up of an inner surface 93 and an outer surface 95. The radius of curvature of inner surface 93 is slightly less than the radius of curvature of outer surface 95, with the result that the wall is relatively thick, typically 0.75 mm., at point 97 near where the wall meets flat portion 57 to base 53, and relatively thin, typically 0.25 mm., at point 99, where the wall joins top portion 65. Top portion 65 and sidewall 63, along with base 53, form a pumping subchamber in which the base and top are flat and oppositely disposed. The wall 63 is everywhere an arch of decreasing thickness toward the top portion, with the inner surface 93 being substantially smooth to avoid accumulation of infusate material and the formation of air bubbles. Also, an important distinction over the rolling diaphragm type pump chambers is that the subchamber wall is self-supporting and does not collapse under negative gauge pressures likely to be encountered in the patient care environment, which are typically in the range of 0 to 100 torr or more. It should be appreciated that other sidewall designs contemplated by the invention may not be so stout. However, as a practical matter, the sidewall should be able to withstand a negative gauge pressure of at least 15 torr, preferably at least 30 torr, and more preferably at least 100 torr, in order to avoid collapse if the patient should move or change position.

It should also be noted that for this preferred embodiment that the geometry itself is quite different from rolling diaphragm type systems. If one looks at a cross-section of the inner surface 93 taken through the center of the axis of revolution of the subchamber, hereinafter the Z-axis, the slope of the inner surface 93 which is located to the right of the Z-axis has a slope $\leq 0$ and the portion of the inner surface 93 which is located to the left of the Z-axis has a slope $\geq 0$, and on neither side does the slope change sign, i.e. the second derivative is less than or equal to zero.

Another way to describe this preferred geometry is that in a relaxed state a plane tangent to any point on the inner surface of the wall would contact the inner surface of the chamber volume at only one point. Further, in the more general case, where the inner surface of the wall is not so smooth as the inner surface in this preferred embodiment, a more general statement of the description is that a plane tangent to the neutral surface of the wall would contact the neutral surface of the chamber at only one point. The term "neutral surface" is used here in the sense of structural mechanics, i.e. the neutral surface is that surface between the inner and outer surfaces which exhibits no stress when the wall is bent.

Another important feature is the fact that displacement of the cap causes stress to be distributed throughout all portions of the arched sidewall. Also, the resulting strain energy as a result of these stresses is a function of displacement, creating a substantially springlike response. This is quite unlike the rolling diaphragm sidewalls wherein the stresses are localized in the rolling convolution, the strain energy remaining substantially constant as the sidewall is displaced.

The advantages of the preferred design of the subchamber are several. As already indicated, the supported base, supported top, and tapering side wall provide a self-supporting structure resistant to expected changes in pressure in an operating infusate system, for either positive or negative pressures. Special precautions against collapse of the pumping chambers in the event of negative pressure, such as may be caused by a mobile patient, are not needed. Moreover, the shape of a chamber after a pumping stroke is precisely restored, increasing the accuracy of the pumping, and inadvertent overpressure conditions (such as might be encountered in set-up and purging) cannot damage the flow chamber, thus avoiding danger to the patient.

The unique tapering sidewall shape of this preferred embodiment offers a further advantage illustrated in FIG. 7 and FIG. 8. FIG. 7 shows the subchamber at full volume and FIG. 8 shows the same subchamber depressed. In depressing the chamber, maximum bending of sidewall 63 occurs where the sidewall meets top portion 65, i.e. where the sidewall has a minimum thickness, thereby requiring the least work to flex to the position of FIG. 8. Minimum bending is at the base where the wall thickness is a maximum. The result is an effective compromise that provides the subchambers with stiffness to reduce volume compliance, and also makes them flexible enough to minimize the pumping force required.

Figure 10:
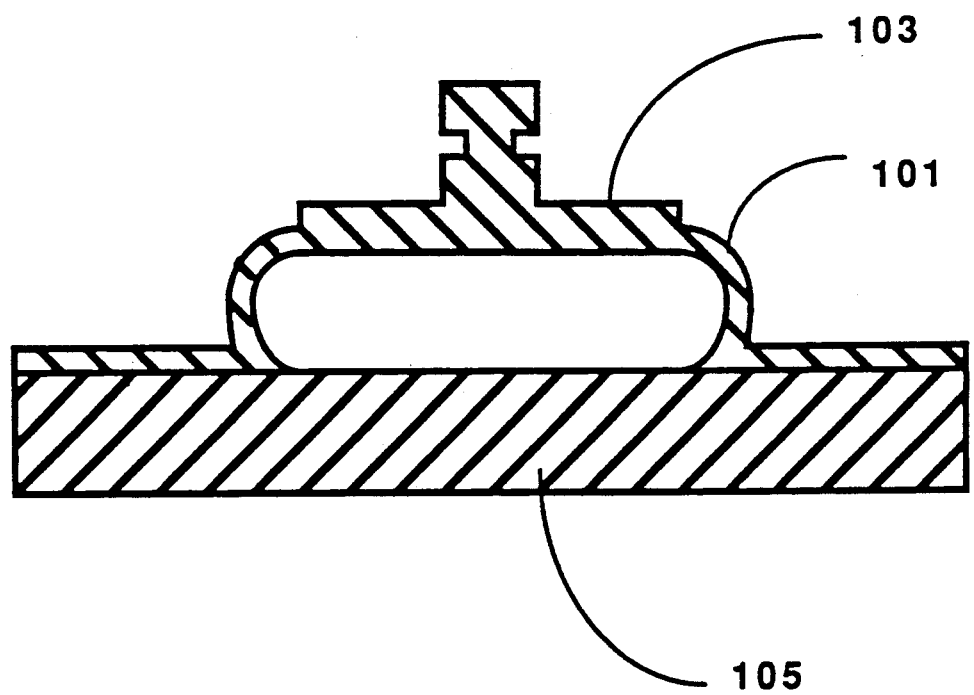
FIG. 10 (A) illustrates an alternative embodiment of a subchamber for the disposable flow chamber of FIG. 2.
Figure 10:
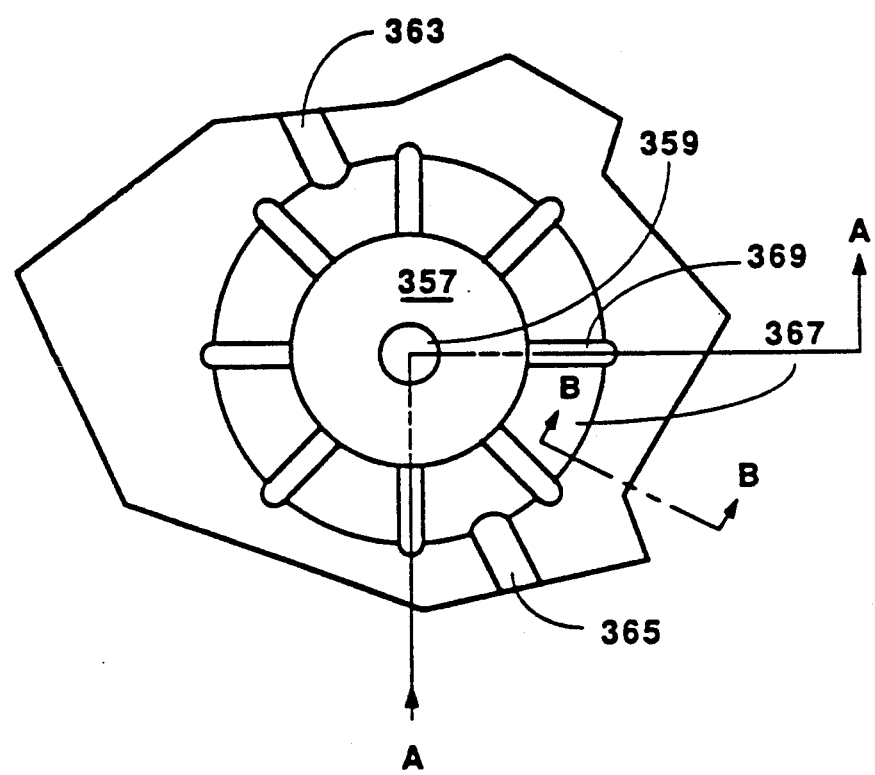
Figure 10:
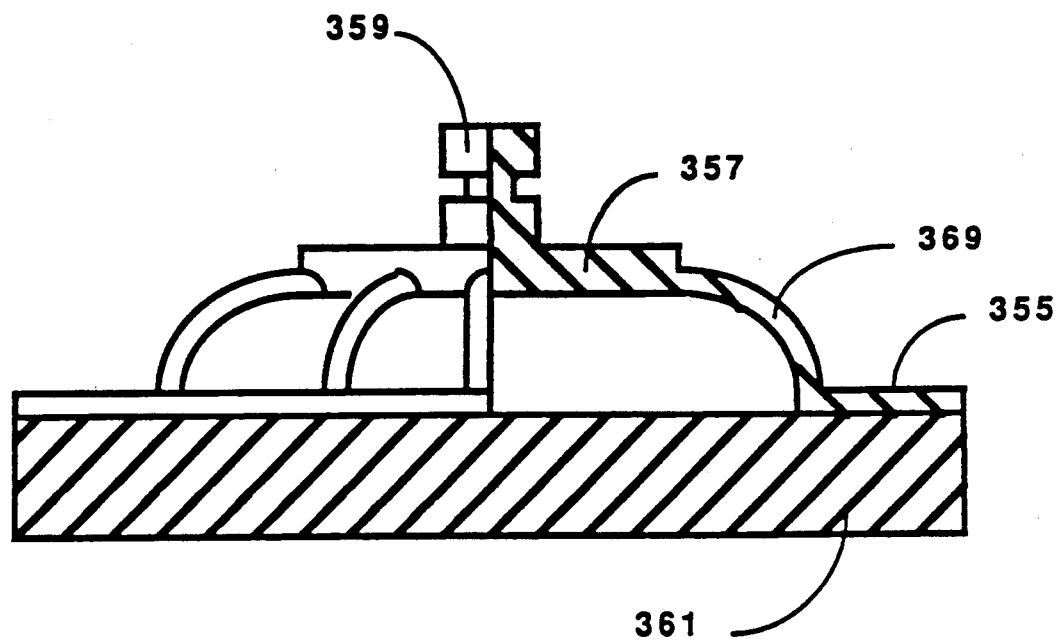
Figure 10:
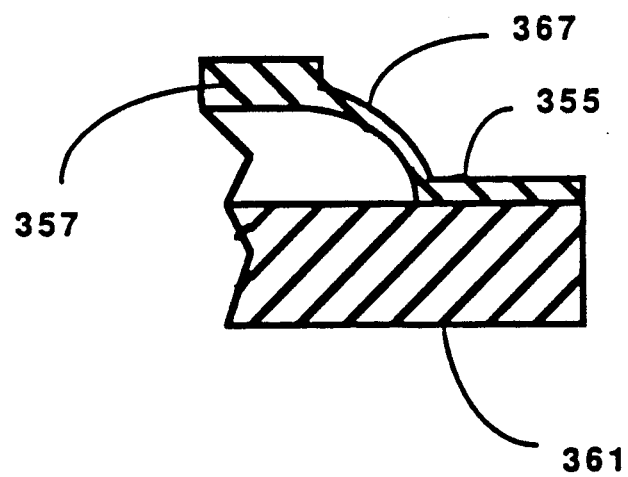
Figure 10:
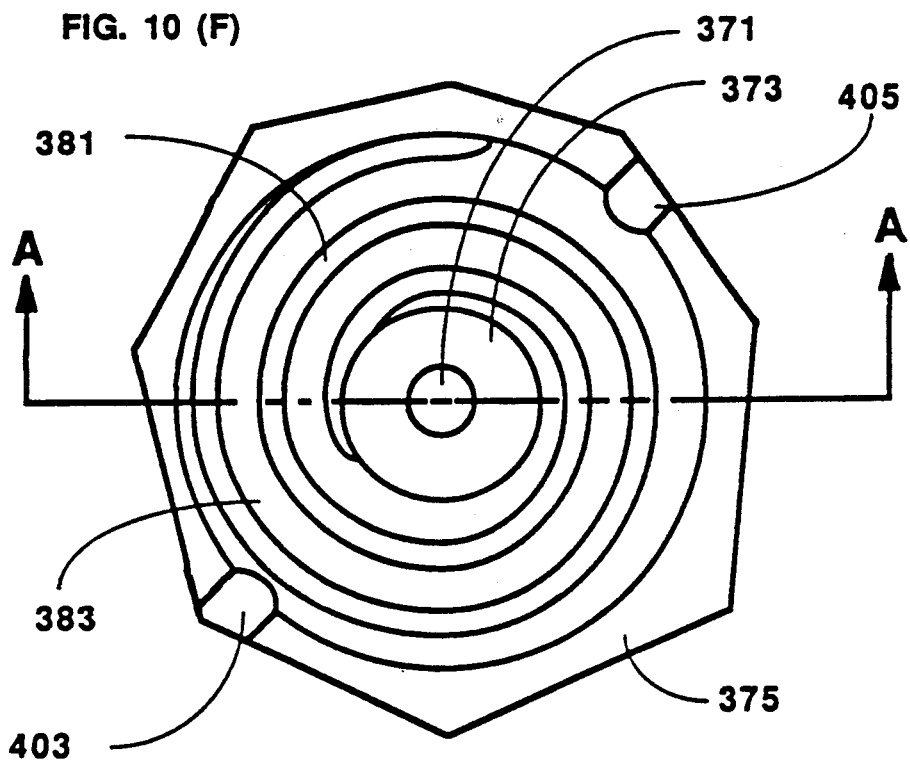
Figure 10:
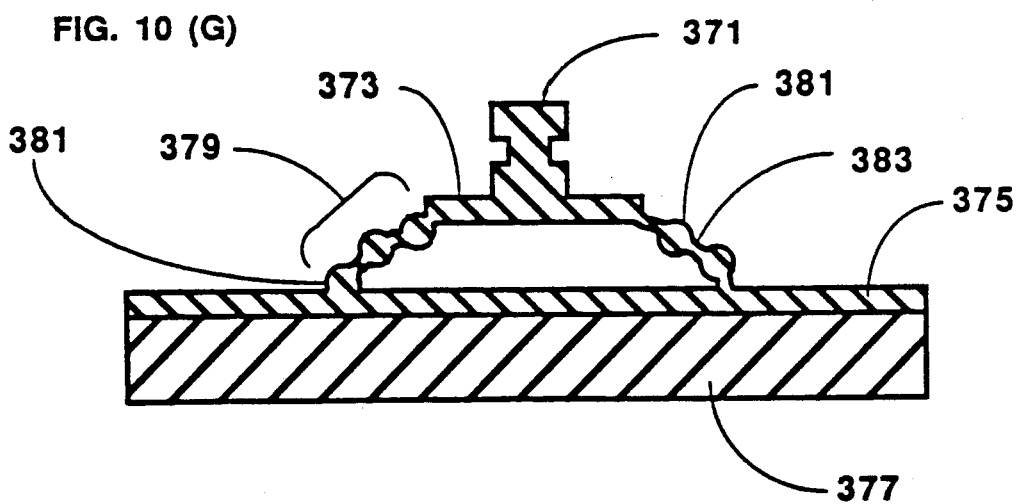
Figure 10:
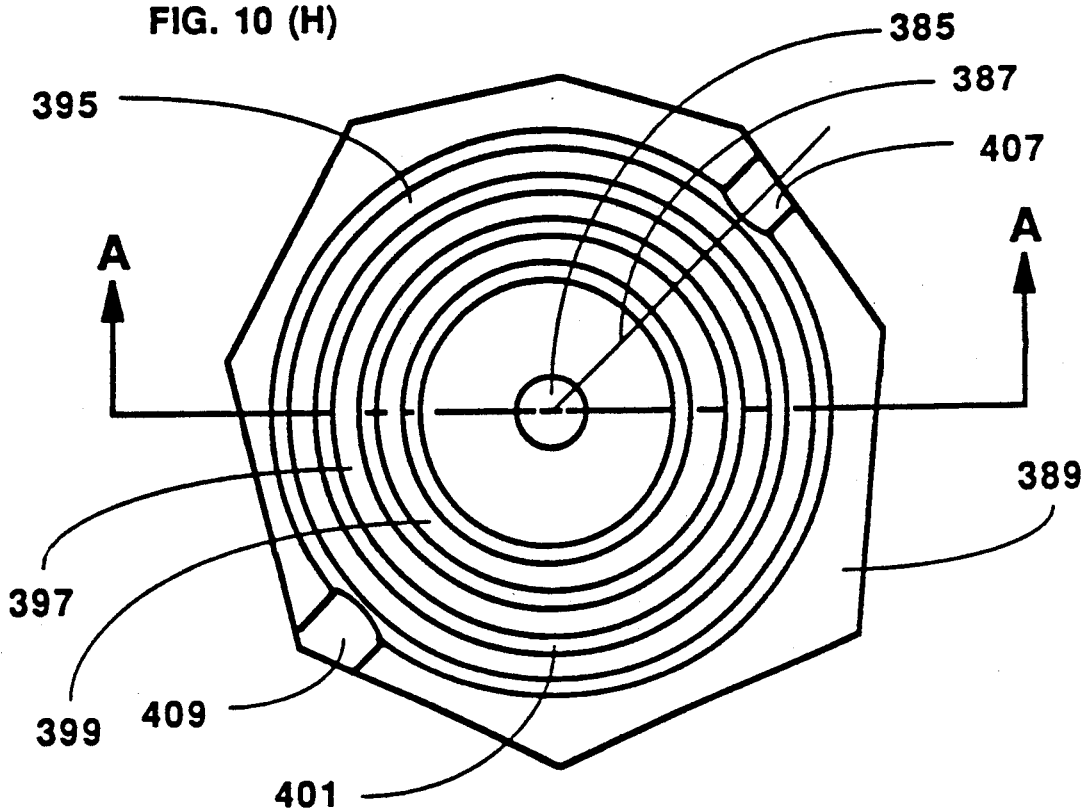
Figure 10:
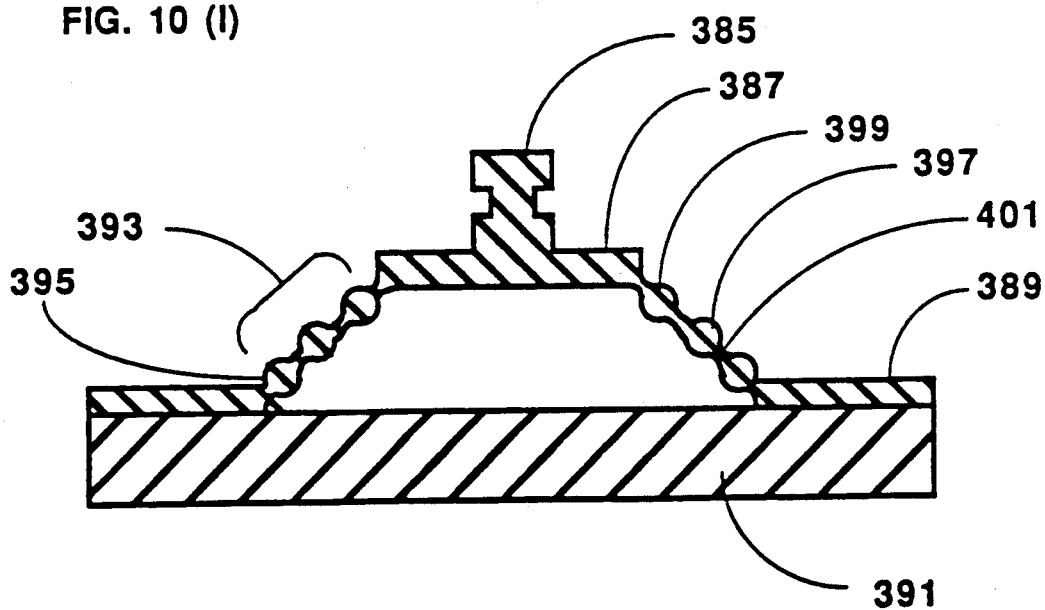

In an alternative embodiment of disposable flow chamber 15, the sidewall portions 63 of the subchambers may be of constant wall thickness, retaining most of the advantages described above. In another embodiment the top portion 65 may be of the same thickness as the side walls, rather than thicker and more rigid than the side walls, and a thicker, more rigid top portion, with or without a connector nib 67, may be added by heat sealing or by joining with adhesive, among other methods. In yet another embodiment shown in FIG. 10(A), sidewall 101 of a subchamber may be a circular arch of further arched extent than the approximately 90 degree arches thus far described, so the slope of the sidewall may change sign one time in the arched extent from base 105 to top 103. In the embodiment of FIG. 10(A), sidewall 101 may be of constant thickness or the thickness may vary to some degree.

FIG. 10(B) shows yet another embodiment of a subchamber for a disposable flow chamber. In this embodiment there is a top portion 325 equivalent to top portion 65 of the first-described preferred embodiment, with a connector nib 335 equivalent to connector nib 67. Flat portion 339 is equivalent to portion 57 in the preferred embodiment, shown in FIG. 6 and base portion 341 is equivalent to base portion 53. Sidewall 343, extending from top portion 325 to flat portion 339 is altered from the previously described embodiments. Two horizontal ring sections, upper section 345 and lower section 347 make up sidewall 343. The right half of FIG. 10(B) is a section view to show the cross-section of the wall shapes, and the left half is not sectioned to show the aspect of the outer wall as made up of joined horizontal rings. Upper ring section 345 joins top portion 325 at a relatively thick point 349, and lower ring section 347 joins flat portion 339 at relatively thick point 351. The two ring sections join one another at relatively thin point 353. A typical thickness at points 349 and 351 is 1.25 mm., and a typical thickness at point 353 is 0.25 mm., although these dimensions may be varied to alter certain functional characteristics of the flow chamber. When the subchamber of FIG. 10(B) is manipulated as a pump or a fill chamber, elastic deformation takes place most readily at point 353 and less readily at points 349 and 351. Other embodiments may be formed by changing the relative thicknesses of the wall members and the thickness at the points where wall members join. These dimensions will determine how the subchamber in such embodiments will collapse under the influence of a connecting rod. Still other embodiments can be formed by changing the number and the dimensions of such horizontal rings making up the sidewall of a subchamber. The shape of a depressed subchamber, which determines the remaining inner volume in the depressed state, can be controlled by changing the number of horizontal rings and the thicknesses of the rings and the joining sections making up a sidewall. The force required to depress the subchamber and the stored energy in the depressed state may be controlled by the same changes.

FIG. 10(C) is a top plan view of yet another embodiment for the subchamber. FIG. 10(D) is a side view of FIG. 10(C) with a quarter section removed along section line A—A, and FIG. 10(E) is a partial section of a wall of the subchamber of FIG. 10(C) along section line B—B. The subchamber of FIG. 10(C) has a flat portion 355 equivalent to portion 57 of the preferred embodiment shown in FIG. 6. There is a top portion 357 equivalent to top portion 65 of that preferred embodiment, a connector nib 359 equivalent to nib 67, and a base portion 361 equivalent to base portion 53. There are connecting collapsible passageways 363 and 365 shown leading to and from the subchamber. The principal alteration from the preferred embodiment is again in the design of the sidewalls. In the embodiment shown by FIG. 10(C) the sidewall is a thin membrane supported by vertical ribs. One of eight thin membrane sections thus formed is section 367, and one of eight rib sections is rib section 369. Section lines A—A and B—B were chosen to show the cross-sections of a typical rib and a typical thin membrane section respectively. The force required to depress the subchamber and the stored energy in the depressed state can be controlled by altering either or both the number of ribs and the cross-sectional area and relative width and thickness of supporting rib sections.

FIG. 10(F) shows yet another alternative embodiment of a sub-chamber for a disposable flow chamber. There is a top portion 373 equivalent to top portion 65 of the preferred embodiment and a connector nib 371 equivalent to nib 67. Flat portion 375 is equivalent to portion 57 of the preferred embodiment, and base portion 377 is equivalent to portion 53. Sidewall 379 differs from previously described embodiments.

FIG. 10(G) is a cross section of FIG. 10(F) taken along section line A—A, and shows the molded construction of the sidewall of the subchamber for a disposable flow chamber is shown by FIG. 10(H) and FIG. 10(I). This embodiment is similar to the embodiment of FIGS. 10(F) and (G), and the differences are again in the integrally molded parts of the sidewall. Instead of the spirally wound rib-spring of FIGS. 10(F) and (G), there are shown three circular ribs; 395, 397, and 399; separated in the sidewall by relatively thin wall sections of which section 401 is typical. There may be one or two such circular ribs or more than three. The purpose is the same as described for the embodiment of FIGS. 10(F) and (G), and the rib and thin section shapes and thicknesses may be tailored to control the collapsed shape of the sub-chamber and the forces required for its operation. The embodiment of FIGS. 10(H) and (I) has elements equivalent to the elements of the other described sub-chamber embodiments, including connector nib 385, top portion 387, flat portion 389, base portion 391 and sidewall 393.

It will also be apparent to those skilled in the art of designing and manufacturing medical devices that all or many of the advantages of the present invention will be retained if changes in the above described designs are made, such as arranging the collapsible passageways so that fluid may enter and exit at other points in the subchambers, such as through base 53 or through top portion 65, rather than through side wall 63; or such as re-arranging the layout of molded subchambers and passageways so that the flow of infusate is not direct along a straight line through disposable flow chamber 15, but by a more circuitous route, changing direction one or more times; or by altering the shape of aforesaid subchambers, which have been described as circular, to another shape, such as oblong or oval. Similarly, other means of attaching the subchamber to the drive rod can be used other than a nib and retaining ring.

FLOW CONTROLLING MECHANISM

Figure 11:
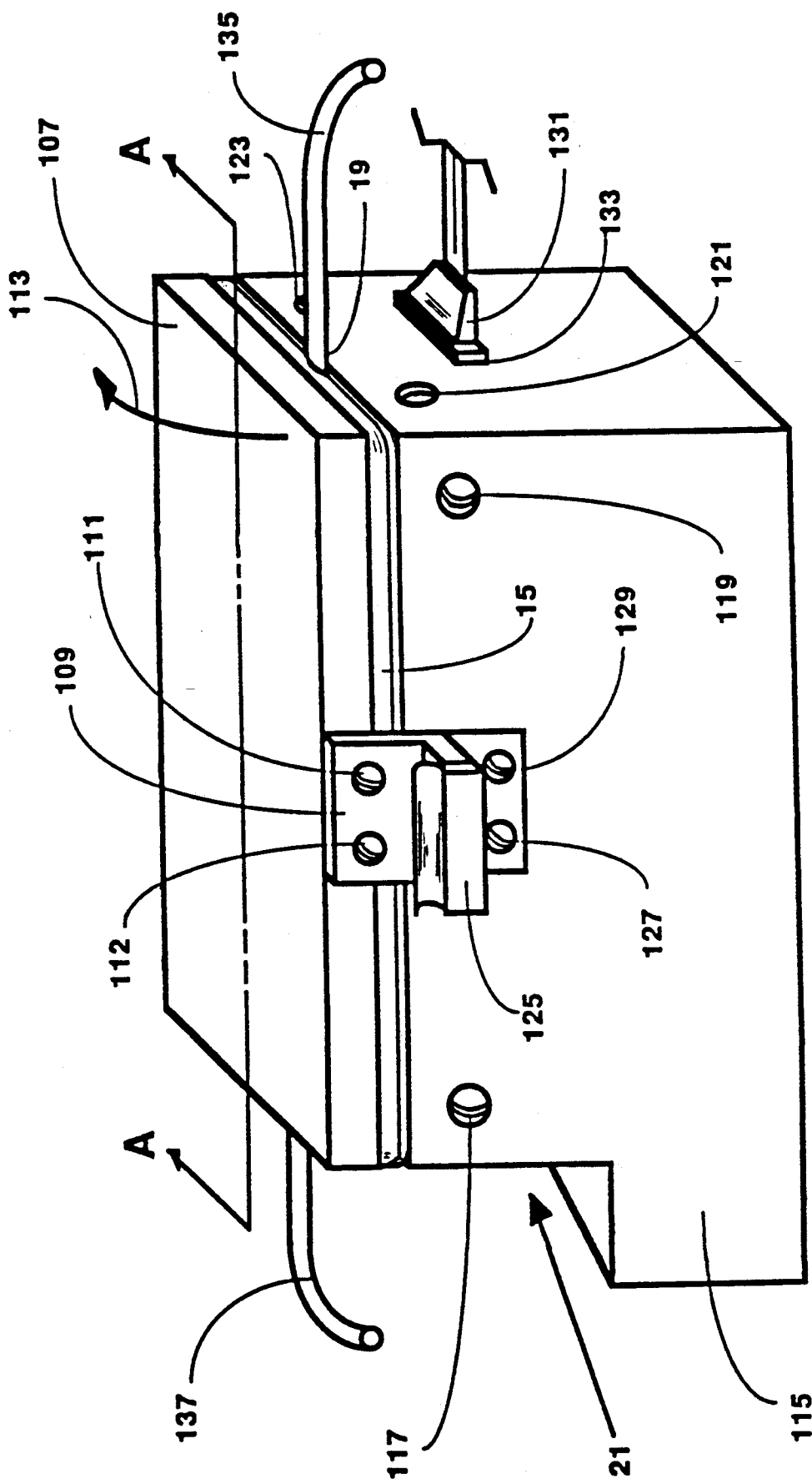
FIG. 11 is a perspective view of a flow control mechanism for causing pumping action with a disposable flow chamber in a preferred embodiment of the invention.

FIG. 11 is a perspective view of flow control mechanism 21, which is a mechanical device for manipulating the above described disposable flow chamber 15 to provide and control flow of infusate in the various embodiments of the invention. Flow control mechanism 21 includes a top cover 107 with a latch plate 109 fixedly attached by screws 111 and 112. The top cover is preferably transparent, made of a medically compatible and rigid material such as acrylic or polycarbonate, and is mounted to an internal member of flow mechanism 21 by hinges not shown, so that the top may pivot open in the direction of arrow 113. Lower parts of the flow mechanism are enclosed by a cover 115 held to an internal frame member by fasteners 117, 119, 121, and 123. The cover may be made of sheet metal, such as stainless steel, and unpainted, or may be of a medically compatible plastic material, among other choices. In the preferred embodiment, cover 115 is a thin piece of opaque plastic, and fasteners 117, 119, 121, 123 and others not shown are stainless steel button head screws.

A latch 125 is fastened to the lower cover by screws 127 and 129 so that when top 107 is closed it will remain closed and will require an effort to open. An electrical connector 131 is shown mounted to an electrical receptacle 133. This connection provides an electrical interface for power and control signals between flow control mechanism 21 and external power supplies and controllers not shown. Workers in the medical equipment arts will recognize that the cover, fasteners, latch and the electrical connector and recepticle may vary widely in shape, material and nature without deviating from the scope and spirit of the invention. Furthermore, due to the fact that only a small amount of power is required to operate flow control mechanism 21, a battery pack can be integrated into the unit rather than having to rely on external power sources.

Disposable flow chamber 15 is shown in FIG. 11 immediately below transparent top 107 between the top and the lower parts of mechanism 21. A flexible tubing 135 described earlier in relation to the flow chamber extends from outlet end 19 of disposable flow chamber 15. The tubing is fixed by heat sealing, by adhesive, by solvent bonding, or by other suitable technique to outlet 19, and as described earlier, acts as the flow passage for infusate to the patient from flow chamber 15. A similar tubing 137 joins to inlet end 17, not shown, and acts as the flow passage for infusate from a reservoir and drip chamber not shown. Such tubing is generally not attached to the apparatus until it is to be used by a patient.

Figure 12:
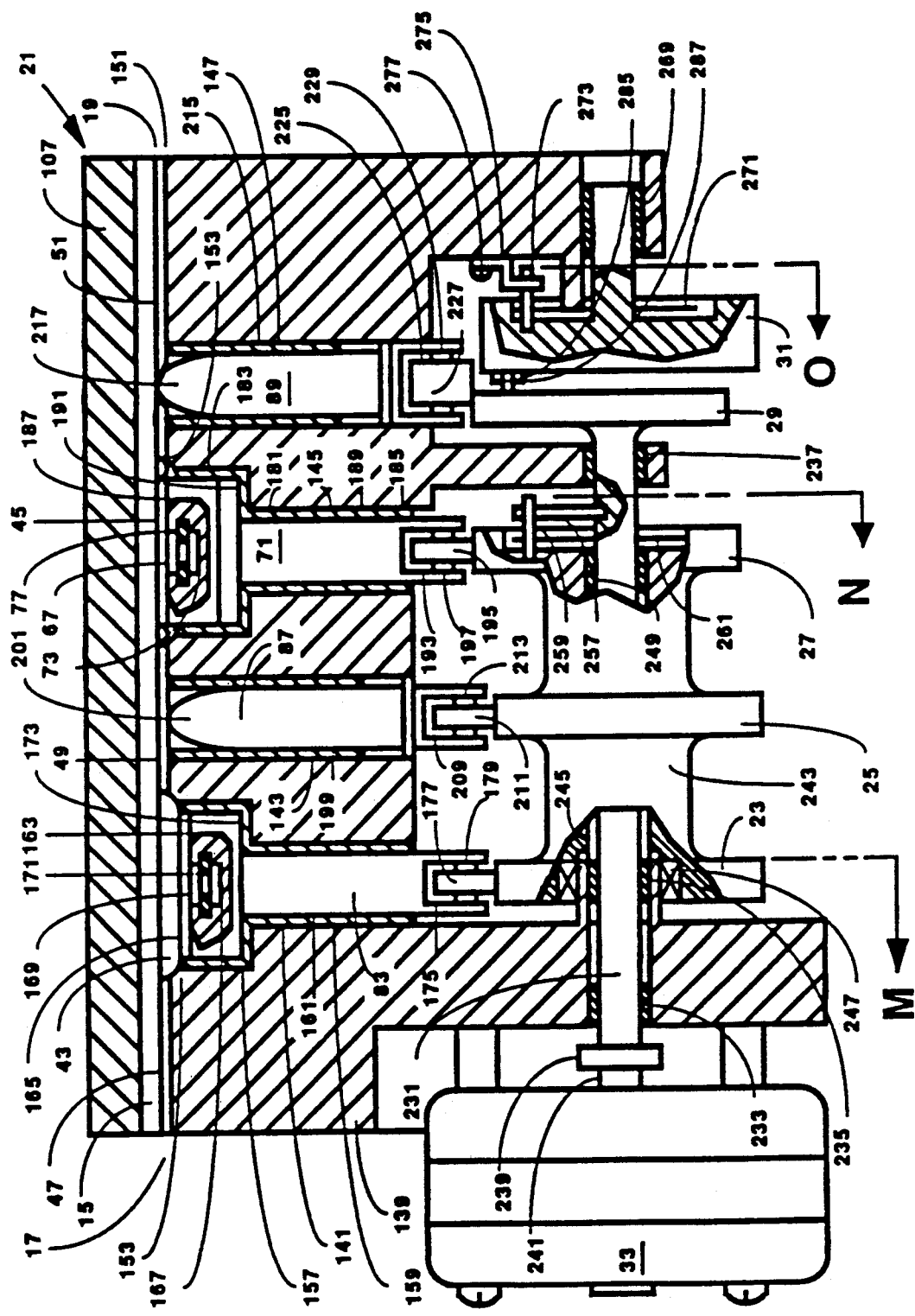
FIG. 12 (A) is a longitudinal section of the flow control mechanism of FIG. 11.

FIG. 12A is a section view through flow mechanism 21 and disposable flow chamber 15 along line A—A of FIG. 11, not including tubing 135 and 137, cover 115 and associated fasteners, or electrical control or power wiring or connectors. FIG. 12A and subsequent views illustrate the design and operation of preferred embodiments of flow control mechanism 21 of the present invention. In FIG. 12A, transparent top cover 107 is shown closed with disposable flow chamber 15 held firmly between the top cover and mostly flat top surface 151 of a frame body 139 which is the main frame member of flow control mechanism 21. Disposable flow chamber 15 is oriented with fill and pump subchambers 43 and 45 one above the other as shown in FIG. 1, the preferred orientation during operation, although they can be operated in other orientations as well. For purposes of discussion, however, the following description of the flow control mechanism will be described as if the flow chamber 15 is in a horizontal orientation as illustrated in FIG. 12(A). Inlet end 17 appears at the left and outlet end 19 appears at the right, and collapsible passageways 47, 49 and 51 are illustrated as well. Frame body 139 is preferably a molded member made of a rigid plastic material such as nylon or other engineering plastic, although other materials may be used, including metals.

Four bores 141, 143, 145 and 147 are molded vertically into or machined through frame body 139. Bore 141 is at a position and of a cross-section such that fill subchamber 43 of flow chamber 15 will fit comfortably therein. Bore 145 accomodates pump subchamber 45 in a similar manner. At the opening of bore 141 proximate top surface 151 where flow chamber 15 mounts, wall 153 is machined or molded to have the arch shape of sidewall 65 of fill chamber 43. (Arched sidewall 65 is shown in FIG. 6.) Upper portion 155 of bore 145 is shaped similarly to fit the curvature of pump chamber 45. This curvature provides extra support for the respective subchamber walls in the event of overpressure conditions inside flow chamber 15. Below curved wall 153, bore 141 has two diameters in the preferred embodiment. Upper portion 157 is the larger of the two diameters and lower portion 159 is the smaller. Both upper and lower portions can be lined with bearing material 161 such as filled teflon or bronze, if desired.

Connector rod 83 is fitted into bearing lined bore 141 in a manner such that the connecting rod may freely move in a vertical direction but is restrained in rotation and motion in all other directions. Connector rod 83 has a large diameter end 163 which is the same diameter as semi-rigid top 165 of fill subchamber 43. The connector rod has a hole 167 which accepts nib 169 of subchamber 43, and fastens thereto in assembly by means of spring retainer ring 171. Oppositely disposed grooves in hole 167 and nib 169 have sufficient clearance, and spring retainer ring 171 sufficient movement, along with the resilient material of nib 169, that connection may be conveniently made by pushing nib 169 into hole 167 by pressure applied on the opposite side of flow chamber 15.

The vertical length of upper portion 157 of connector rod 83 is such that with the fill chamber 43 in its normal, uncompressed, as-molded condition, connector rod 83 rests on shoulder 173 in lined shaft 141. At the lower end of connector rod 83 there is a slot 175 into which a cam follower 177 is mounted on a shaft 179 so that the follower may freely rotate about shaft 179 which spans slot 175. Although the upper portion of rod 83 in contact with semi-rigid top 165 of subchamber 43 is shown to be the same diameter as top 165, in some instances it may be desirable to use a rod 83 that does not have such an expanded upper portion 157, for example to facilitate assembly of the apparatus.

Bore 145 of subchamber 45 is also lined with a bearing material 181 and contains connector rod 71. In the preferred mode, the assembled parts of the pump subchamber 45 are in every way similar to the assembly at bore 141; including connector rod 71, lining 181, large diameter bore portion 183, lower small diameter bore portion 185, large diameter connector end 187, small diameter connector end 189, center hole 73 in top end of connector rod 71, connector nib 67 of pump subchamber 45, spring retainer ring 77, shoulder 191 in bore 145, slot 193 in lower end of connector 71, cam follower 195 in slot 193 and shaft 197 through cam follower 195. In the preferred mode, the upper diameter of both bore 141 and bore 145 is about 2.5 cm, and the lower diameter of each bore is about 1.0 cm.

Bore 143 through frame body 139 is a single diameter bore of about 1.0 cm diameter lined with bearing material 199 similar to bore 141 and 145. Bore 143 is centered directly below collapsible passageway 49 of flow chamber 15 about half the distance between fill subchamber 43 and pump subchamber 45. Valve closure rod 87 is fitted into lined bore 143 in a manner providing free movement vertically but restraining movement in other directions. Valve closure rod 87 has a blunt end 201 immediately below passageway 49. The design of the system is such that when the rod is not supported or forced toward the disposable flow chambers, the flow pressure and the small force provided by spring-like restoring force of passageway 49 will be sufficient to ensure that rod 87 will retract from passageway 49 allowing the passageway to open. A slot 209 contains a cam follower 211 similar to followers 177 and 195, rotatable on shaft 213 which spans the slot. When urged in the upward direction valve closure rod 87 closes collapsible passageway 49 of flow chamber 15, preventing flow from fill subchamber 43 to pump subchamber 45. Clearly, return springs also could be used to bring the rod back to its home position, if desired.

Bore 147 has a bearing lining 215 and is positioned under passageway 51 of disposable flow chamber 15 about half way between pump subchamber 45 and outlet end 19. An assembly of parts in bore 147 acts as a valve closure upon passageway 51 as above described for bore 143 and passageway 49. The parts include bearing lining 215, valve closure rod 89 with blunt end 217, cam follower slot 225, cam follower 227, and cam follower support shaft 229. Valve closure rod 89 closes passageway 51 and returns in the manner above described for valve closure rod 87. An important difference is in cam follower 227 which is sufficiently wide to span two cams at once, cam 29 and cam 31.

In this preferred embodiment, connector rods and valve closure rods are moved in their respective bearing lined bores by a series of five rotatable cams including fill cam 23, transfer valve cam 25, pump cam 27, exit valve cam 29 and exit valve servo cam 31. All of these cams are driven by a single motor 33, although not always together or in the same rotating direction. A drive shaft 231 extends most of the length of flow control mechanism 21 and is supported rotatably in frame body 139 by journal bearings 233, 235 and 237. Cam 29 is fixedly attached to drive shaft 231 at one end, and is the only cam fixedly attached to the drive shaft. The other end of drive shaft 231 is attached to a coupling 239 which is in turn attached to motor shaft 241 of motor 33. As a result of this arrangement, exit valve cam 29 will always rotate in the same direction as motor 33. Fill cam 23, transfer valve cam 25 and pump cam 27 are all part of a single triple cam assembly (TCA) 243. The TCA has an internal bore 245 larger in diameter than drive shaft 231 and is bored on one end to receive an over-running clutch 247. TCA 243 mounts on over-running clutch 247 to frame body 139 on one end, and to drive shaft 231 on journal bearing 249 on the other. TCA 243, as well as the other cams, 29 and 31, are preferably made of a tool steel to resist wear, but because of the very light loads encountered, may also be made of other materials, including engineering plastics.

Figure 13:
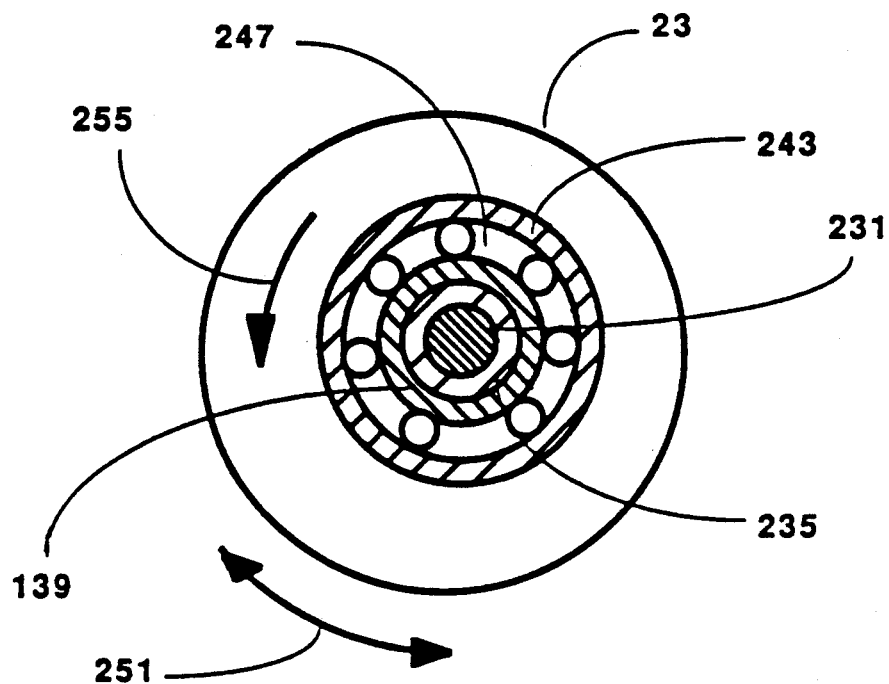
FIG. 13 is a section view through section line M of the triple cam assembly of FIG. 12 (A) showing mounting to a drive shaft with an over-running clutch.

FIG. 13 is a section through TCA 243 at line M of FIG. 12A, adjacent to fill cam 23, looking in the direction of the arrow at M. Drive shaft 231 can rotate, driven by motor 33, in either rotary direction, indicated by arrow 251. Bearing 235 is a journal type bearing such as made and sold by Boston Gear Works and others, and does not restrict rotation. Frame body projection 139 does not rotate. Over-running clutch 247 is a one way rotation device such as a Type FC Drawn Cup Roller Clutch made by Torrington Co., a division of Ingersoll-Rand Corporation. This arrangement provides that TCA 243 will only rotate in the counter-clockwise direction of arrow 255 when viewed along the drive shaft length toward the motor end, and can never rotate in a clockwise direction.

At the opposite end from the over-running clutch, TCA 243 mounts to drive shaft 231 on a journal bearing 249 as before described, similar to bearings 233, 235 and 237. At the end of TCA 243 adjacent journal 249 there is an arrangement of a pin 257 fixedly attached into drive shaft 231, and a pin 259 fixedly attached into TCA 243 and a coil wound spring 261. (see FIG. 14).

Figure 14:
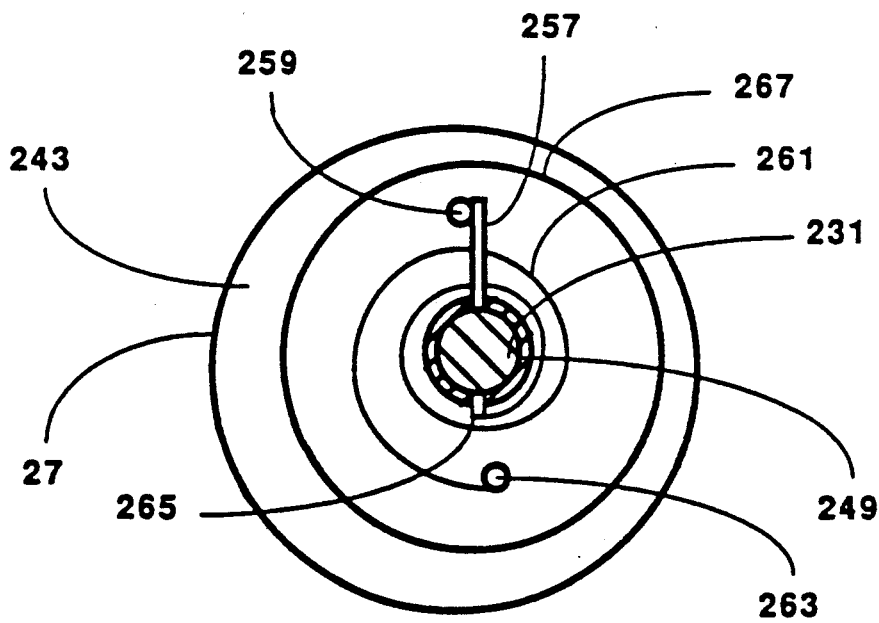
FIG. 14 is another view through section line N of FIG. 12 (A) showing how the triple cam assembly is moved by the drive shaft.

FIG. 14 is a section view through drive shaft 231 at line N looking in the direction of the arrow at N. As previously described pin 257 is fixed in drive shaft 231, while pin 259 is fixed in TCA 243. Coil spring 261 is assembled in machined recess 267 in TCA 243, one end fixed at point 265 to drive shaft 231, and the other end to pin 263 into said TCA; the coil prewound so that spring force is applied rotatably to cause pins 257 and 259 to be urged together. When drive shaft 231 is rotated by motor 33 in a counter-clockwise direction pin 257 drives TCA 243 through pin 259 so that the members rotate together as if a single element. If drive shaft 231 stops, TCA 243 also stops. When drive shaft 231 is rotated clockwise by motor 33, TCA 243 cannot follow, because of the over-running clutch 247 of FIGS. 12 and 13, so pin 257 rotates away from pin 259, TCA 243 remaining stationary, and spring 261 applies torque urging TCA 243 against the resistance of the over-running clutch.

As illustrated in FIG. 12A, at the end of frame body 139 opposite motor 33, on the same centerline as drive shaft 231, servo cam 31 is mounted in journal bearing 269. A coil spring 271 is mounted from frame body 139 to cam 31 and a pin 273 is fixedly attached to cam 31 in a manner that it may interfere with a stop bracket 275 fastened to frame body 139 by screw 277.

Figure 15:
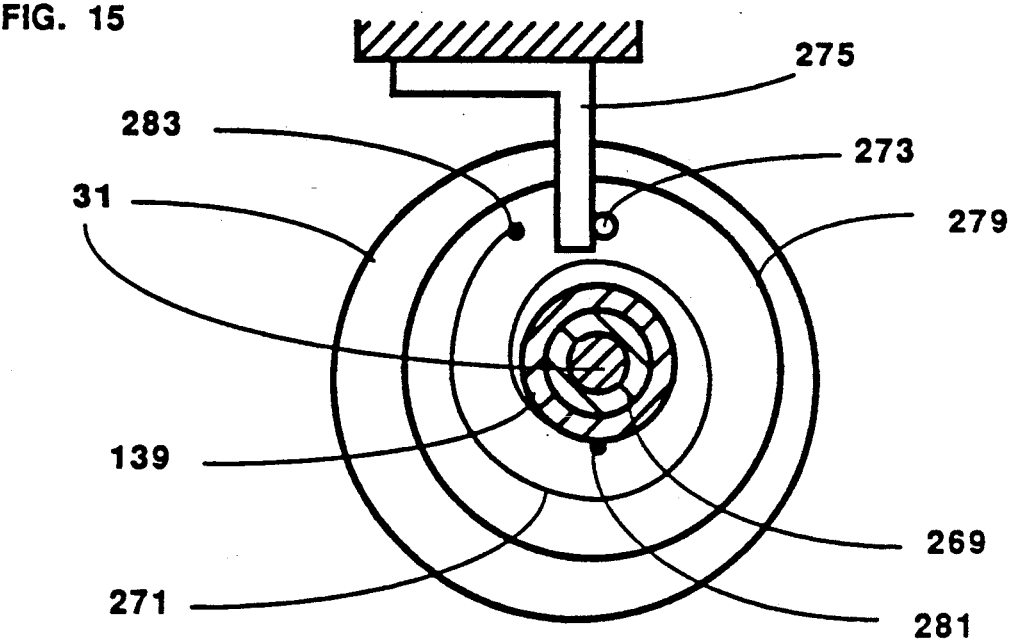
FIG. 15 is another section from FIG. 12 (A) showing mounting and operation of a servo cam.

FIG. 15 shows the arrangement from a section view at line 0, in the direction of arrow at 0. Pin 273 is fixed in cam 31. Coil spring 271 is attached at point 281 to frame body 139 and at the opposite end to pin 283 fixed in cam 31, the spring prewound and having a sufficiently large spring constant to urge servo cam 31 to rotate in a counter-clockwise direction when looking in the direction of motor 33. Cam 31 can rotate counter-clockwise only until pin 273 contacts stop bracket 275.

Exit valve cam 29 has a pin 285 fixed on the side facing servo cam 31, and the cam has a spring pawl 287 at the same radius as pin 285 and facing cam 29. This arrangement is illustrated in FIG. 12A as well as in FIG. 16, which is an enlargement looking between the cams from the approximate vantage point of cam follower 227. When exit valve cam 29 rotates counter-clockwise, the top of the cam moves in the direction of arrow 289. Pin 285 moves in the same direction. Spring pawl 287 is a flat leaf spring member attached to exit servo cam 31 at point 291. Servo cam 31 cannot move in counter-clockwise direction 289 because of pin 273 and stop 275, shown also in FIG. 15. As cam 29 rotates counter-clockwise, pin 285 will cam over pawl 287 with the pawl flexing away from pin 285, offering little resistance to movement of cam 29. If cam 29 stops and then rotates clockwise, in the direction of arrow 293, pin 285 will engage pawl 287 without the pawl springing away, and servo cam 31 will rotate with exit valve cam 29 in a clockwise direction, the spring urging the pawl and cam to remain together.

FIG. 12(B), a partial view of FIG. 12(A), shows portions of connector rods 83 and 71 below frame body 139 and above the cams. FIG. 12(C) is a section view taken through FIG. 12(B) at section line A—A viewed in the direction of the arrows. These views are considerably enlarged to show detail and parts not shown in FIG. 12(A). FIG. 12(B) and FIG. 12(C) show a hinged beam arrangement for the preferred embodiments by means of which connector rods 83 and 71 are caused to act in concert rather than independently. As illustrated, connector rod 83 has a slot 319, and connector rod 71 has a similar but oppositely disposed slot 307. A one piece beam member 295 has a first rounded end 303 that fits into slot 319 of connector rod 83, and a second rounded end 305 that fits into slot 307 of connector rod 71. The hinged beam has a central hole with a bearing 301 by which it is mounted on a shaft 297 which is fixedly attached to an extension 299 of frame body 139. The pivoted arrangement of hinged beam 295 constrains the vertical movements of connector rods 83 and 71 so that movement in either direction by one of the rods is accompanied by the exact movement in the opposite direction by the other, and a force in one direction on one connector rod will always be transferred through the hinged beam arrangement into a force in the opposite direction on the other connector rod. The design of slots 319 and 307 is such that there will neither be interference nor relative motion between the hinged beam and either of the connector rods as the limited vertical motions required for operation are performed.

The cams and drive train arrangements of flow control mechanism 21 above described are such that the fill and pump subchambers are manipulated for pumping and the valve closure rods are moved to cause closure of collapsible passageways 49 and 51 by rotation of motor 33. Rotation counter-clockwise, looking toward the motor, turns drive shaft 231 in the same direction, and exit valve cam 29, fixed to drive shaft 231 will rotate as well. Pin 257 and 259 will cause TCA 243, with cams 23, 25 and 27 to also rotate counter-clockwise. In this mode cams 23, 25, 27 and 29 all operate together and manipulate disposable flow chamber 15 to act as a precise volumetric pump, moving infusate from inlet end 17 to outlet end 19 periodically. Fill cam 23 operates connecting rod 83 through follower 177, moving top 165 of fill subchamber 43. Transfer valve cam 25 moves valve closure rod 87 through follower 211 causing passageway 49 to open and close. Pump cam 27 operates connecting rod 71 through follower 195 moving top 65 of pump subchamber 45. Exit valve cam 29 moves valve closure rod 89 through follower 227, opening and closing passageway 51. The sequence of these operations is as above-described with reference to FIG. 9 for disposable flow chamber 15, occuring in the sequence of six phases per cycle.

In the pumping action of manipulating flow chamber 15, the hinged beam arrangement plays an important role in the preferred embodiment to maximize energy efficiency. When a fill or pump subchamber is depressed by the action of a connecting rod, much of the work is stored as potential energy in the flexure of the subchamber wall; and as drive shaft 231 continues to rotate, the energy is recovered to perform work on the connector rod moving downward, thus potentially achieving a more efficient design. The hinged beam arrangement transfers the force during movement to an upward force at the other end, thereby, making it possible to recover a portion of the stored energy. This efficiency is further enhanced by not having to use return springs for the connecting rods.

Figure 17:
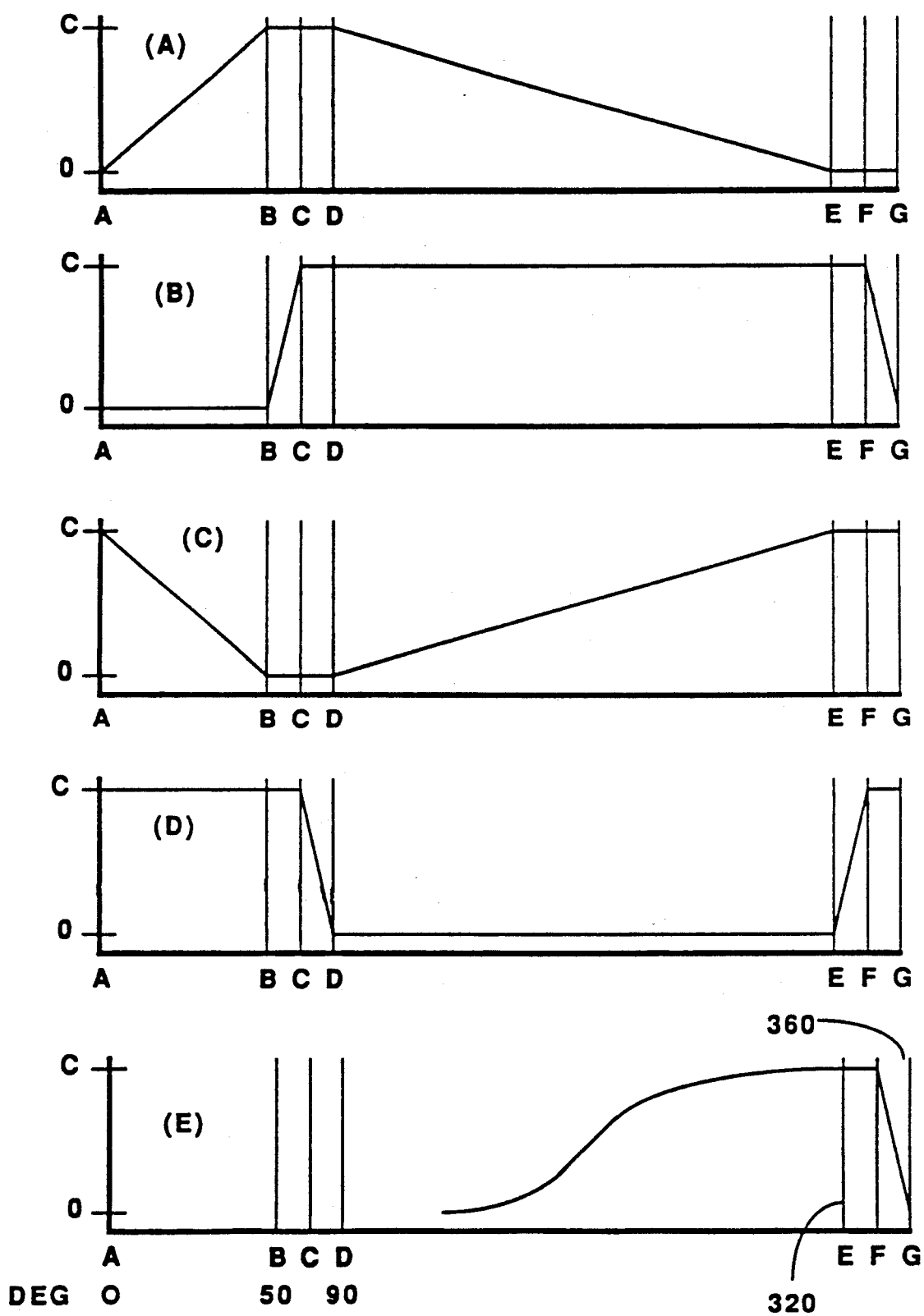
FIG. 17 (A) is a cam profile for a fill cam of the flow control mechanism.

FIGS. 17A–17E show approximate cam profiles for all five cams of flow control mechanism 21. The ordinate for each profile represents relative cam displacement and the abcissa is angular displacement from zero degrees at point A to 360 degrees at point G, which is point A returned. FIG. 17A represents the profile for fill cam 23 in the preferred embodiment, B for transfer valve cam 25, C for pump cam 27, D for exit valve cam 29 and E for exit servo cam 31.

The home position at angular position A has fill cam 23 retracted. Fill subchamber 43 is thus at normal uncompressed position at point A; transfer valve is open; pump subchamber 45 is fully depressed and exit valve is closed. As counter-clockwise rotation proceeds to angular position B the fill subchamber depresses, transfer valve remains open, pump subchamber 43 goes to uncompressed position and the exit valve remains closed. From B to C the transfer valve closes. From C to D the exit valve opens. From D to E, which is an angular rotation of about 230 degrees, the fill subchamber returns to full uncompressed volume and the pump subchamber compresses. This action draws infusate from tubing connected to a reservoir, into the fill subchamber, and moves an identical volume of infusate over the same time span from pump subchamber 45 to the tubing to the patient. From E to F the exit valve closes, and from F to G, which is back to A, the transfer valve opens. The approximate angular positions are indicated at the bottom of FIG. 17E for each phase, A through G.

During counter-clockwise rotation, exit servo cam 31 does not rotate, and flow control mechanism 21 operates as a precise volumetric pump.

If rotation is stopped at angular position G, passageway 49 is open and flow poassage 51 is closed. If rotation of cam 29 is reversed at this point, TCA 243 remains motionless, spring pawl 287 and pin 285 engage, and servo cam 31 rotates clockwise with exit valve cam 29. As illustrated in FIG. 12A, exit valve cam 29 and exit servo valve cam 31 will each operate follower 227 in sequence and hence valve closure rod 217 operates on passageway 51. The home position of sevo cam 31 during pump operation (counter-clockwise), which position is maintained by spring 271, pin 273 and stop 275, is a position in which the land of the cam is below the lowest point of cam 29, so follower 227 never makes contact with cam 31 during pump operation.

Reference to FIGS. 17(A)–17(E) will show that reverse (clockwise) rotation from point G will result in servo cam 31 making contact with follower 227 by the time point F is reached. Continuing reverse rotation of cams 29 and 31 from point F will have cam 29 fall away from follower 227, but the position of closure rod 89 will be controlled by cam 31. The opening of passageway 51 under the control of cam 31 will be gradual, requiring a rotation of less than about 230 degrees to full open at angular position D, and the relative amount of opening will vary monotonically with the degree of rotation of servo cam 31 from angular position F to angular position D. The concept is to provide positive control of flow over the entire range of 230 degrees, which in this preferred embodiment means providing accurate flow rates from as low as 5 ml/hr to as high as 1000 ml/hr. The gentle roll of the cam profile shown in FIG. 17(E) helps to accomplish this desired control.

Flow control mechanism 21 thus operates both as a volumetric pump and as a drip-rate controller. Steady rotation in a counter-clockwise direction causes action as a precise volumetric pump. Rotation in the reverse direction controls the position of valve closure at passageway 51, and such rotation may be stopped at any point, providing a choice of positions from fully open to fully closed. In operation as a drip rate controller impetus to flow is provided by a pressure head as a result of elevation of an infusate reservoir and drip chamber above the elevation of the mechanism 21 and the patient. The drip rate, hence flow rate, in the drip-rate mode is a function of the opening of passageway 51 by valve closure rod 89, which is in turn a function of the degree of rotation of cam 31.

Figure 16:
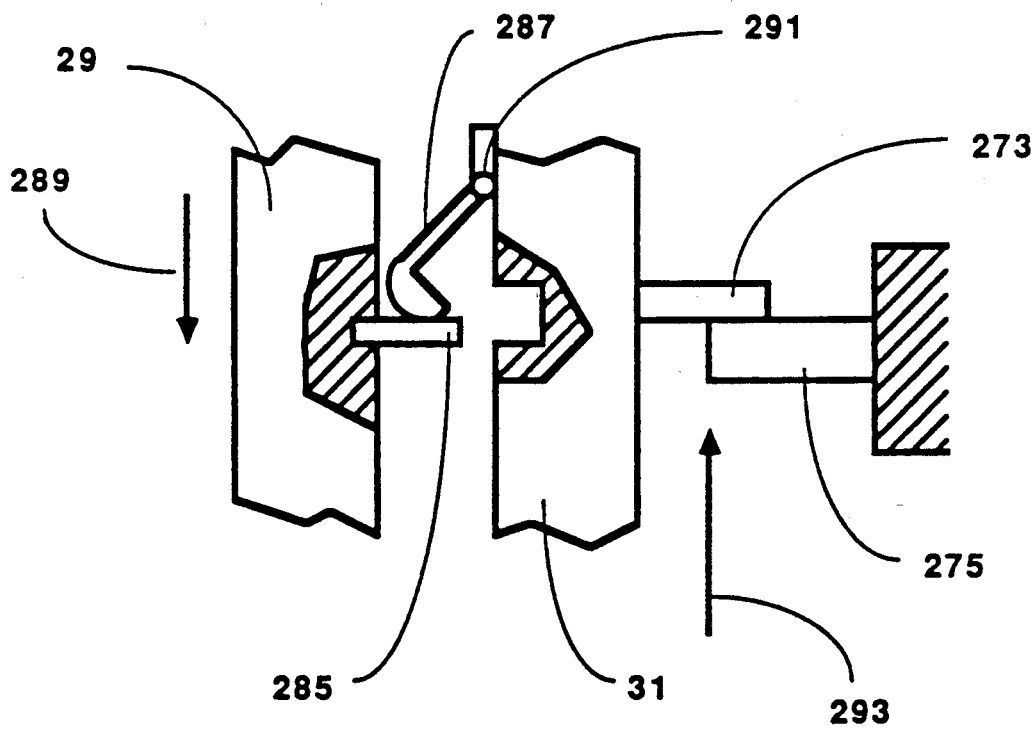
FIG. 16 is an enlarged plan view of the servo cam and an exit valve cam illustrating a spring latch drive arrangement between the two.

As an alternative embodiment of flow control chamber 21 the spring pawl arrangement of FIG. 16 is not used. In that embodiment, an extension of drive shaft 231 can be made to project through exit valve cam 29 and into a central hole in exit servo cam 31. A one way clutch, similar to clutch 247 is mounted between cam 29 and cam 31 such that the clutch free-wheels when drive shaft 231 rotates counter-clockwise. When clockwise rotation is initiated, the clutch engages, so cam 29 and 31 rotate together, coil spring 271 ensuring clutch engagement.

In yet another embodiment servo cam 31 is driven by a second motor, separate from motor 33, and for servo operation as a drip rate controller, both motors rotate in unison, motor 33 rotating only enough to clear cam 29 from interfering with position of valve closure rod 29.

Those skilled in the art will recognize that many alterations may be made in the designs, materials and timings of this system without departing from the spirit and scope of the invention. For example, the timing of events represented by cam profiles of FIG. 17 may be altered considerably without seriously effecting the operation. Drive motor 33, preferably a stepper motor, may also be a permanent magnet synchronous motor or a DC shuntwound motor, among other choices. There exists a wide choice of shaft sizes, bearing types and materials, cam followers and the like, to accomplish the functions described. Pivoted beam member 295 of FIGS. 12B and 12C might also be a section of a pinion gear spanning from connecting rod 71 to 83 with a rack section attached to each said connecting rod, the pinion pivotal at a point halfway between the connecting rods. There exist other ways of joining connector rods 71 and 83 so that their opposite movement may be coordinated and the energy used for compression in depressing subchambers of flow chamber 15 may be partially recovered in rotation. Many advantages of the invention are retained even when no pivoted beam is used at all.

INFUSION METHOD

As indicated earlier, FIG. 1 is a schematic diagram showing the infusion pump system of the preferred embodiment. An advantage of the infusion pump system of the present invention is that the pump mode need be used only intermittently, or, in many cases, only at the beginning of an infusion, thereby saving a substantial amount of energy which is used to drive the pump, a very important aspect in the case of battery powered units.

It should also be appreciated that there are many variables that effect drop volume in a drip chamber, such as drop size and shape, type of infusate, atmospheric conditions, temperature, the presence of volatile components in the air, which may effect surface tension of a fluid, and more. Simply counting the number of drops per unit time is not an adequate method for controlling infusions, particularly in cases where the infusate is of a kind that a small amount may have a large effect on a patient, because of slow feedback of drop detecting signals to the controlling mechanism at low rates. Volumetric pumps have been developed to improve the accuracy of infusions, but such pumps in the prior art are prone to problems. They are expensive to operate over long periods, they are energy inefficient, and may not be completely safe for the patient, e.g. due to overpressure. Most, if not all of these problems are eliminated by using the above-described apparatus according to the following method.

Figure 18:
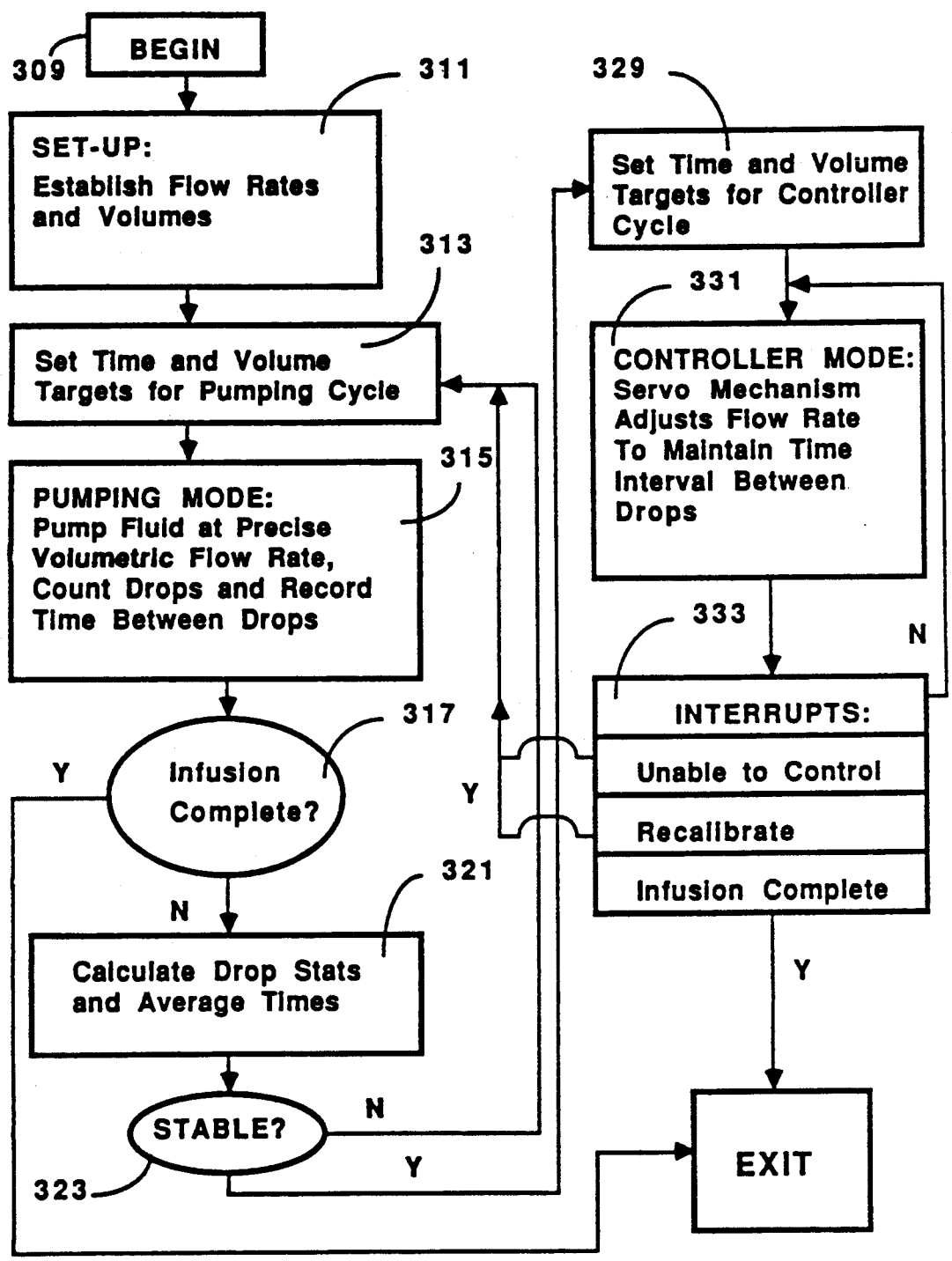
FIG. 18 is a flow diagram of a preferred method of calibrating a passive infusion.

FIG. 18 is a flow chart of a control algorithm as used in the preferred embodiment for a dual mode infusion including both intermittent pumps and a passive calibrated infusion. The method begins at program element 309. At program element 311, the control system, i.e. CPU 39, requires input from the operator in order to set up an infusion sequence. The flow rate desired for the particular case is entered, as well as other information required by the control system program, such as the total volume of infusion, pressure limits, and length of time to operate in the pump mode after infusion begins before switching to controller mode. After setup, control moves to program element 313 to compute and set time and volume targets. At program 315, the pumping mode, pumping proceeds during which time infusate is pumped at a volume rate set by the operator at program element 311. At program element 317, the system tests to see if infusion is complete. If it is complete before the programmed pump mode times out, the system logic proceeds to exit and operation stops. If the infusion is not complete, drop statistics and time intervals are calculated at program element 321. At program element 323, a decision is made as to whether sufficient information was recorded and calculated to perform a controller mode operation with desired accuracy, i.e. is the drop formation stable? If not, the program returns to program element 313, and the pump mode is re-initiated. If the system is stable, the program proceeds to program element 329, and time and volume targets are set for controller mode operation. At program element 331 the system is in the controller mode. Information stored at program element 321 determines the drip rate corresponding to that flow rate. The regulating feature of passageway 51 (i.e. its monotonically varying valve function when actuated by valve closure rod 89) then operates to provide a drip rate corresponding to the exact volume flow rate desired. The drip rate is monitored and the regulating valve 51 is opened further if the drip rate falls below target value, or is closed somewhat if the target value is exceeded. At program element 333 the system tests to see if the controller mode should be interrupted, as illustrated for example if the system flow rate becomes unable to be controlled, if a recalibration is required, or if infusion is complete. For the two former situations, the system is returned to program element 313, i.e. to pump mode operation, which serves to initiate the recalibration process for another possible controller mode operation. If infusion is complete, the system exits the program.

A major advantage of the program-controlled intermittent system is flexibility. The best treatment program for a particular situation can be chosen, among many possible programs. The time of operation in each mode can be widely varied. The precise flow rates available vary across the complete spectrum of flow rates for usual infusates. The system allows operator over-ride so that changes may be made in desired rates and programmed times, as well as in the chosen operating mode, at any point in a program. Typically, the system program of the preferred embodiment stops in a home position of the pump mode such that the valve closure at the outlet end of the flow chamber is closed. The system may be operated in either of the operating modes without alteration, if that should be desirable in a particular case.

The infusion pump system of the present invention provides flexibility for the operator, safety for the patient, low cost, reliable operation insensitive to faults common to other systems, and a potentially low manufacturing cost.

Figure 19:
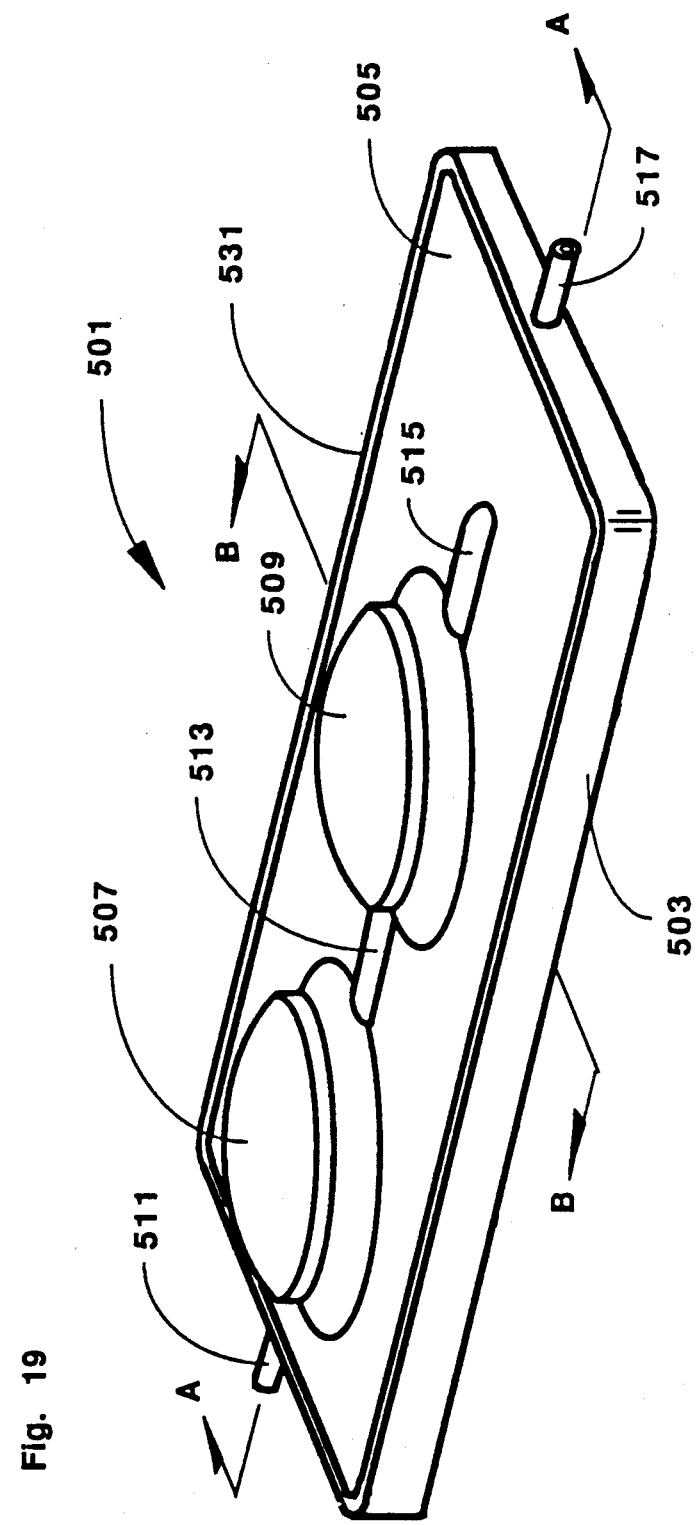
FIG. 19 shows a perspective view of an alternative embodiment of the invention.

In yet another alternative preferred embodiment illustrated in FIG. 19, a disposable flow chamber 501 is shown in which connection of drive elements to the pumping chambers is not required. Chamber 501 comprises a base 503 and a flexible molded portion 505, and there are two pumping subchambers 507 and 509. Base 503 of disposable flow chamber 501 is molded of material that is rigid after molding, such as acrylic or polycarbonate. The rigid base and flexible portion 505 are joined by an adhesive, or, depending upon the materials used, by heat sealing, just as in other embodiments described above. The rigid materials base provides structural integrity as well as ease and accuracy in assembly.

Infusate flow into disposable flow chamber 501 is through a tube 511 projecting from the rigid base, and through a passage in the base into pumping subchamber 507. Flow from subchamber 507 to pumping subchamber 509 is through passage 513 molded into the flexible portion of the flow chamber as in the other described preferred embodiments, and flow out of pumping subchamber 509 is through passage 515, which connects with another passage (not shown) through the rigid base, and out of the disposable flow chamber through tube 517, molded as part of the rigid base. There is an optional internal chamber (not shown in FIG. 19) through which infusate may pass from passage 515 before reaching tube 517.

Figure 20:
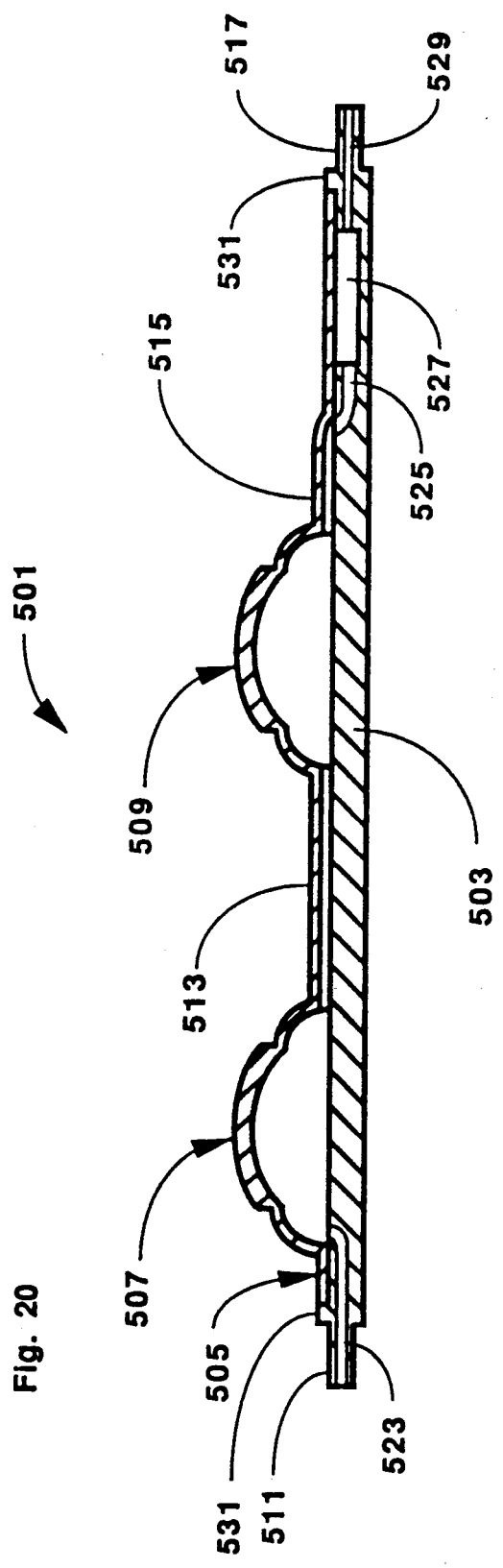
FIG. 20 shows a cross-section of the alternative embodiment of FIG. 19.

FIG. 20 is a section of the disposable flow chamber of FIG. 19 along the section line A—A of FIG. 19. Infusate enters at tube 511 and goes through internal passage 523, molded into rigid base 503, and into pumping chamber 507. Infusate flows from pumping subchamber 507 into pumping subchamber 509 through flexible passage 513. From pumping subchamber 509, infusate flows through flexible passage 515 into internal passage 525, and into optional transducer chamber 527, which may be used to position or mount an instrument such as a temperature or a pressure transducer. From the optional transducer chamber, flow is through internal passage 529 exiting the disposable flow chamber through tube 517.

There is a molded rim 531 around the rigid base in the preferred embodiment, creating a depression in which the flexible portion of the device fits in assembly, further aiding in orientation and alignment. This rim is shown also in FIG. 19.

Figure 21A:
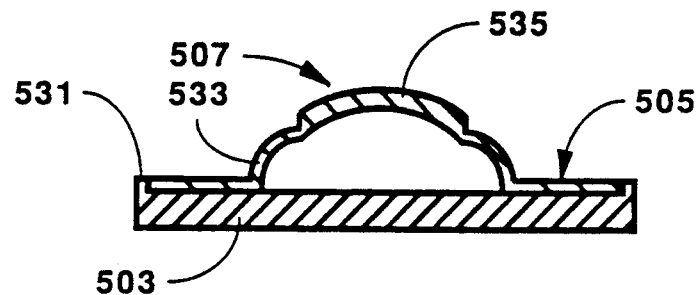
FIGS. 21(a) through 21(c) show a portion of the cross-section of FIG. 20 at various points in the pumping cycle.

FIG. 21(a) is a cross section of the flow chamber of FIG. 19 along the line B—B through pumping subchamber 507. A section through pumping subchamber 509 would be substantially the same. Pumping subchambers 507 and 509, formed by molding in the flexible portion of the flow chamber, have a curved wall 533 of about 1 mm in wall thickness, and a domed portion 535 of about 3 mm thickness. These dimensions may be varied in molding to provide a specific desired spring rate for operation. The outside diameter of curved wall 533 is the greatest diameter of the pumping chamber, and is about 25 mm in the preferred embodiment, while the diameter of domed portion 535 is about 18 mm. The height of wall 533 from the rigid base is about 5 mm, and the overall height of the pumping chamber is about 15 mm, although these dimensions may also vary. The length of the disposable flow chamber is about 10 cm and the width about 4 cm.

Figure 21B:
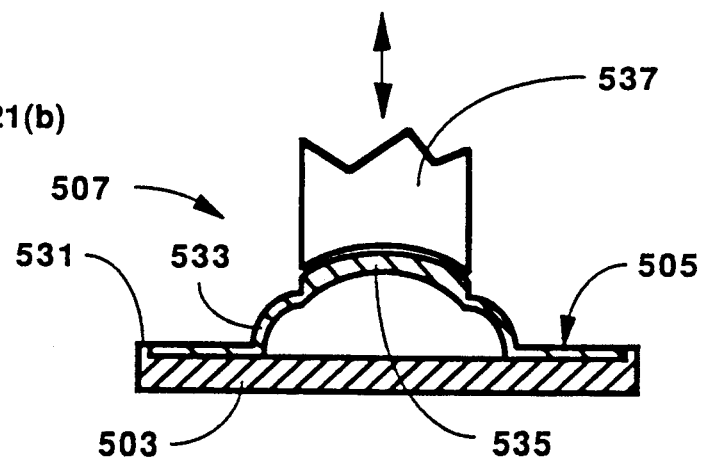

FIG. 21(b) shows the subpumping chamber of FIG. 21(a) with an actuator rod 537 in contact with domed portion 535 of the pumping chamber. The contacting surface of the actuator rod has the same curved shape as the domed portion of the pumping chamber, so there is no tendency for the domed portion of the pumping chamber to be distorted by the pumping action.

Figure 21C:
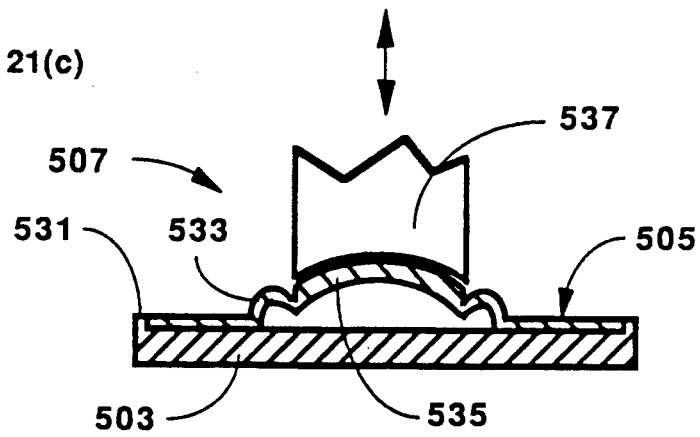

FIG. 21(c) shows the pumping subchamber depressed by movement of the actuator rod. The actuator rod moves the domed portion of the pumping subchamber to force infusate out of the chamber. The movement of the actuator rod causes the volume in the subchamber to decrease, so infusate is forced out of the subchamber. The full extent of the motion of the actuator rod is shown in FIG. 21(c), and is about 5 mm. Curved wall 533 is deformed and provides a resisting force against the actuator rod, so as the actuator rod is withdrawn, the pumping subchamber springs back to its original, undepressed state. The actuator rods for operating the pumping subchambers for disposable flow chamber 501 do not need to be connected to the pumping subchambers as in previously described preferred embodiments. The domed pumping subchamber provides substantial restoring force, more than enough to overcome expected pressure fluctuations in use, by virtue of the wall thicknesses and the design of the walls, which cause compression distortion to take place in actuation as well as bending distortion. In the preferred mode, typically a force of 8 ounces is needed to depress a pumping subchamber of the design of subchamber 507 or 509, although this force may be varied by material formulation, wall thickness, and curvature.

Figure 22:
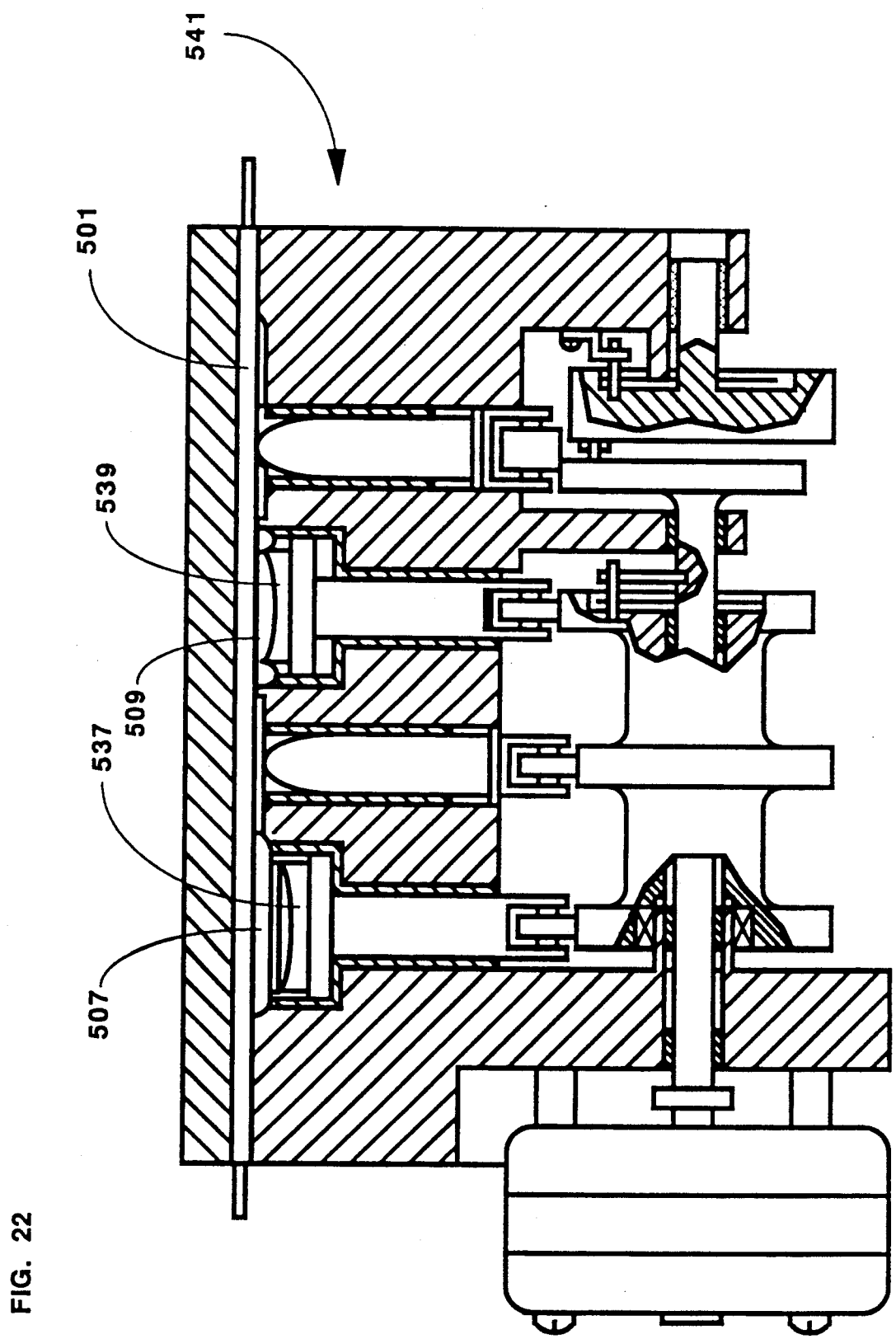
FIG. 22 shows a drive system for operating the alternative embodiment of FIG. 19.

FIG. 22 shows a flow controller 541 similar to the motor-driven flow controller of FIG. 12(A), for use with disposable flow chamber 501. Actuator rod 537 is shown in contact with pumping subchamber 507, and another actuator rod 539 is shown depressing pumping subchamber 509. The actuator rods are not connected to the pumping subchambers, which provides for ease of replacement of the disposable flow chamber. Also, the actuator rods, at the point that they urge against the pumping subchambers, are about the same diameter as the curved portions of the pumping subchambers [See element 535 in FIG. 21(b)], and are also dome-shaped to match the curvature of the pumping subchambers. The design and operation of flow controller 541 is, in other respects than the actuator rods, substantially the same as described relative to the embodiment of FIG. 12(A).

Figure 23:
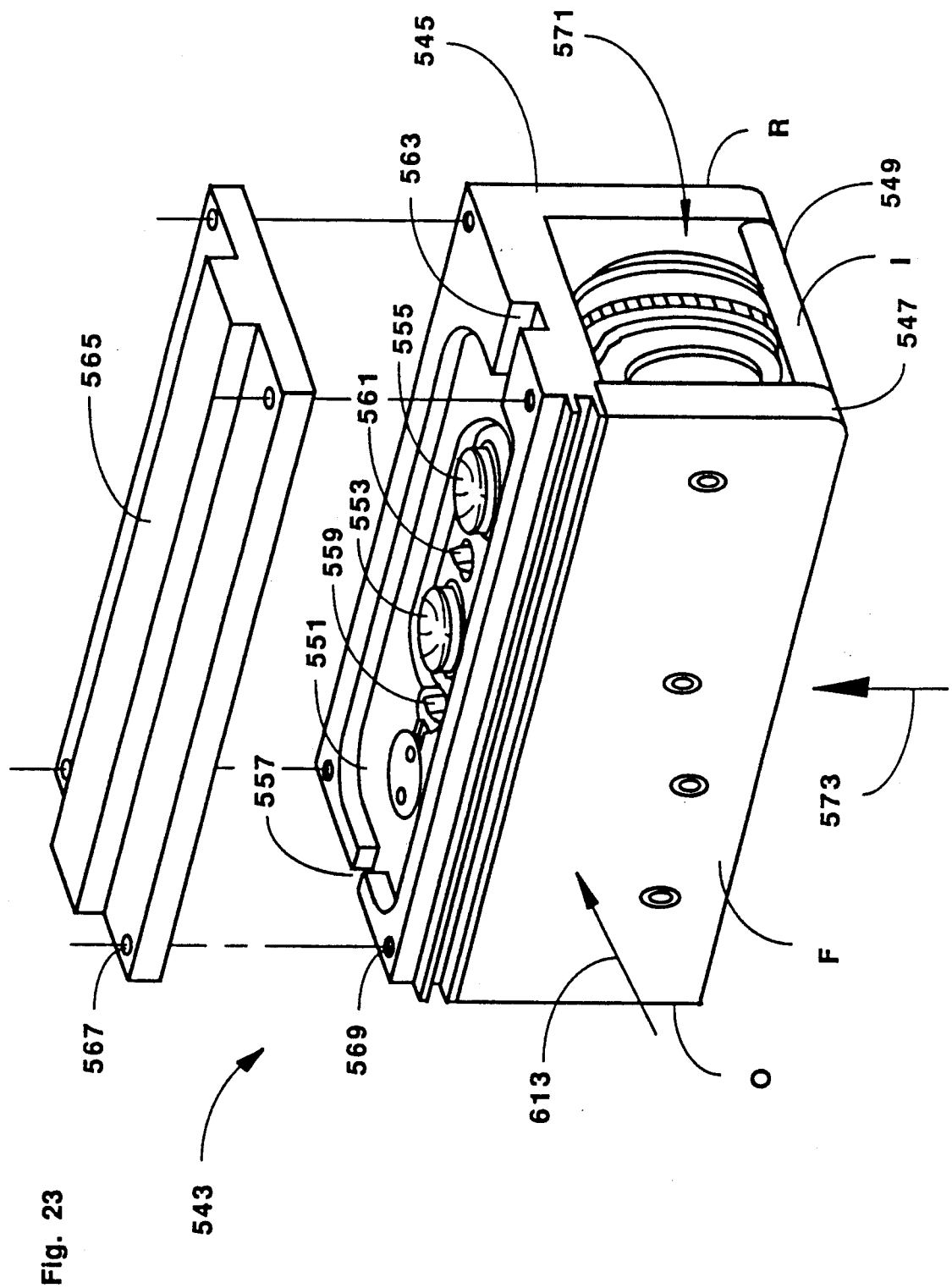
FIG. 23 shows an alternative drive system for operating the alternative embodiment of FIG. 19.

FIG. 23 shows an alternative motor-driven flow controller 543 useful with disposable flow chamber 501. In this preferred embodiment an L-shaped frame member 545 and a second frame member 547 are the main framing elements, connected and spaced apart by spacer-connectors such as element 549. A recess 551 is machined into an upper surface of element 545 to contain and support the disposable flow chamber (not shown in FIG. 23). The disposable flow chamber fits into recess 551 with the domed portion of the pumping subchambers facing downward so that the pumping subchambers engage actuators 553 and 555 of the flow controller. With a disposable flow subchamber 501 (FIG. 20) in place, outlet 517 lies in machined groove 557, flexible passage 515 lies over valve actuator 559, pumping subchamber 509 lies over actuator rod 553, flexible passage 513 lies over valve actuator 561, pumping subchamber 507 lies over actuator rod 555, and inlet 511 lies in machined groove 563. Grooves 557 and 563 are large enough to accomodate flexible tubing attached to the inlet and outlet of the disposable flow chamber, and this tubing is typically attached before a flow chamber is placed in the controller.

The disposable flow chamber is held in position after installation by a top member 565, typically molded of acrylic, polycarbonate, or other rigid flexible material so that the operation of the flow chamber may be viewed with the top member in place. Recess 551 is deeper than the thickness of the disposable flow chamber, and the top member has a machined shape on the underneath (not shown) that fits into the shape of recess 551, providing registration. Conventional fasteners are inserted through holes in the top member and engage threaded holes in frame member 545 to secure the assembly and provide a rigid backing for the operation of both the actuator rods and the valve actuators. Through hole 567 and threaded hole 569 are typical.

Valve actuators 559 and 561 and actuator rods 553 and 555 that operate the two pumping subchambers protrude through holes in member 545 and are driven from below by an electric motor through a series of outside and face-groove cams in a cam group 571, described below, within the controller enclosure.

Figure 24:
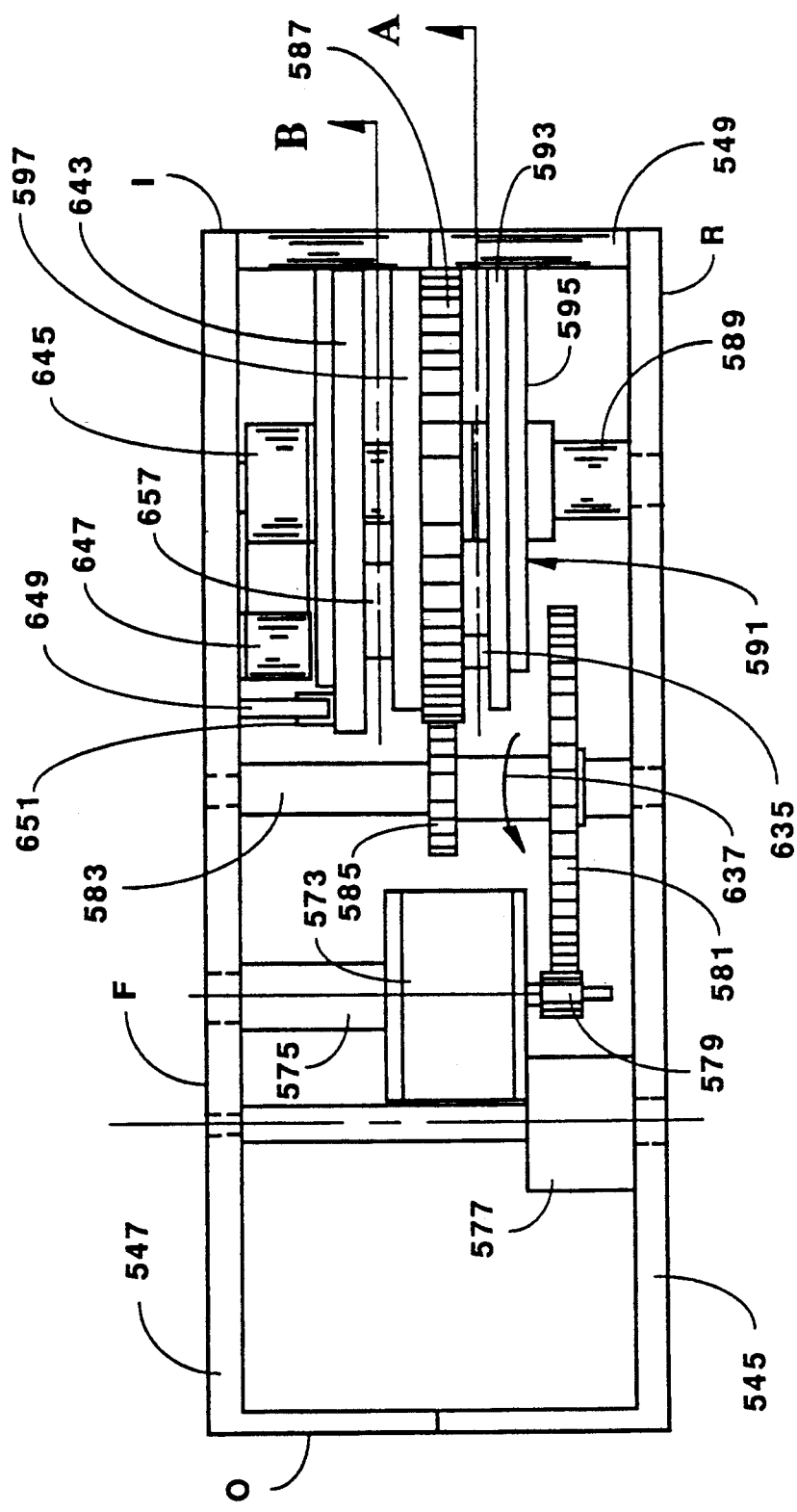
FIG. 24 is a view from the bottom of the embodiment of FIG. 23.

FIG. 24 is a view from the bottom of flow controller 543 (in the direction of arrow 573). The sides and ends of the controller are identified in FIG. 23 as F for front, R for rear, I for inlet end, and O for outlet end, and again in FIG. 24 to aid in maintaining orientation. An electric motor 573, held in place by support members 575 and 577 drives an output pinion 579, which drives a gear 581 on an idler shaft 583. A second gear 585 on the idler shaft, smaller and with fewer teeth than gear 581, engages and drives another gear 587 fixed to a camshaft 589. Cams on the camshaft comprise cam group 571 of FIG. 23. The ratio between gear 579 and 581 in the preferred embodiment is 5:1, and the ratio between gear 585 and gear 587 is 4:1, so the gear reduction from the motor to the camshaft is 20:1.

Cam 591 is a combination cam for driving both actuators 553 and 555 for operating the pumping subchambers, and for driving valve actuator 561 that opens and closes passage 513 betwen the two pumping subchambers. Passage 513 with valve actuator 561 comprises a transfer valve between the pumping subchambers. There are two portions to cam 591 formed from a single piece of stock, typically nylon plastic material. Portion 593 is an edge cam portion. An operating mechanism for the transfer valve follows the outside edge of portion 593, and operates valve actuator 561, moving the actuator vertically through a range of about 2 mm. Portion 595 is a face groove cam. A follower attached to an operating link follows a groove cut into the face of portion 595 and operates both actuators 553 and 555. During operation as a positive flow controller, edge cam 597, attached to gear 587, operates a control link that operates valve actuator 559 to open and close passage 515, providing the exit valve. The followers, operating links, and actuators are not shown in FIG. 24, but are shown in subsequent Figures.

Figure 25:
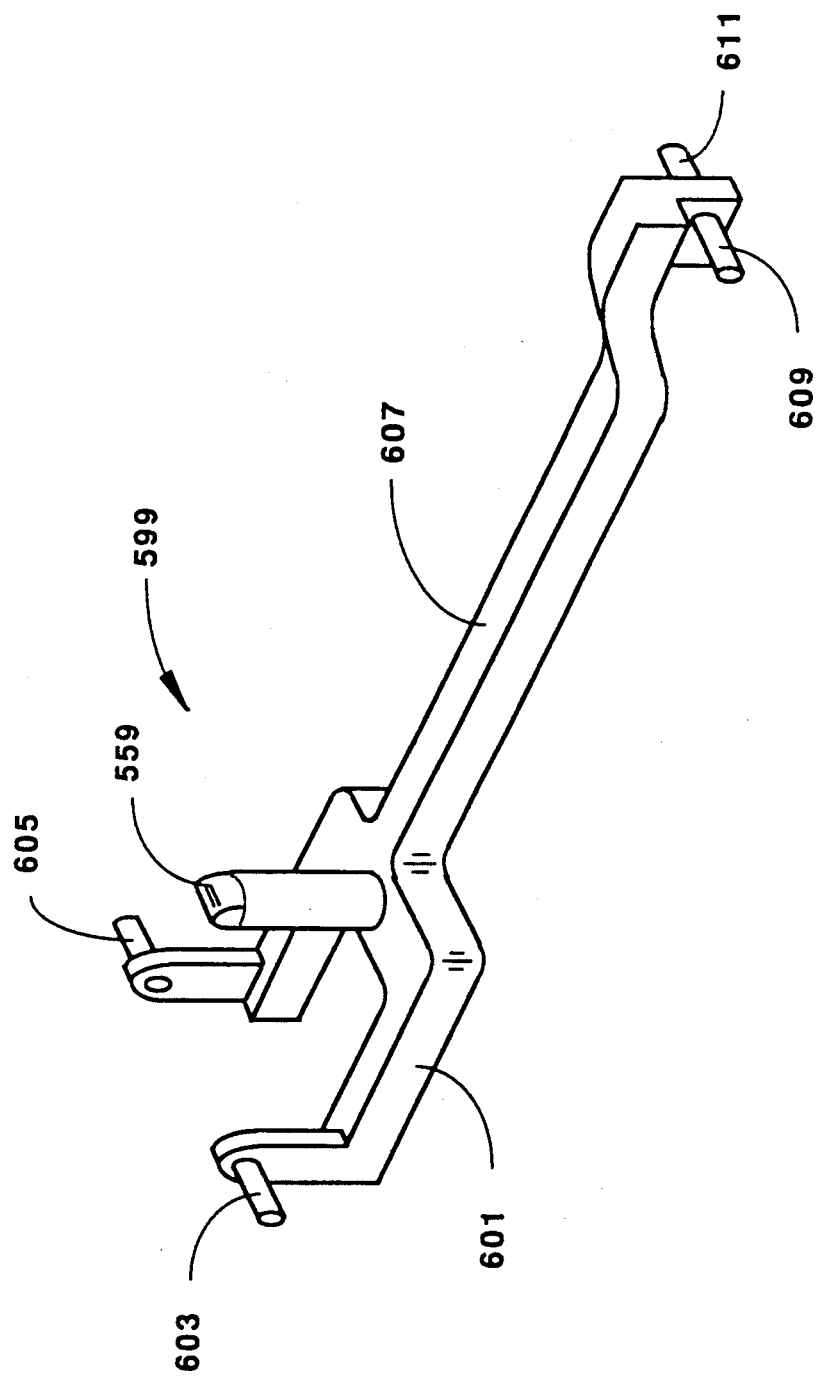
FIG. 25 shows an operating link of the embodiment of FIG. 23.

FIG. 25 shows operating link 599 which operates valve actuator 559 for the exit valve. A yoke 601 has two pivot shafts 603 and 605 that engage pivot holes in the body of the controller. An arm 607 carries cam followers 609 and 611. The followers in the preferred embodiment are plastic bearing material, but could be metal or roller bearings. Follower 611 follows cam 597 to operate link 599 around the pivot shafts, causing valve actuator 559 to move to open and close the exit valve, which in operation acts as a positive flow controller.

Figure 26:
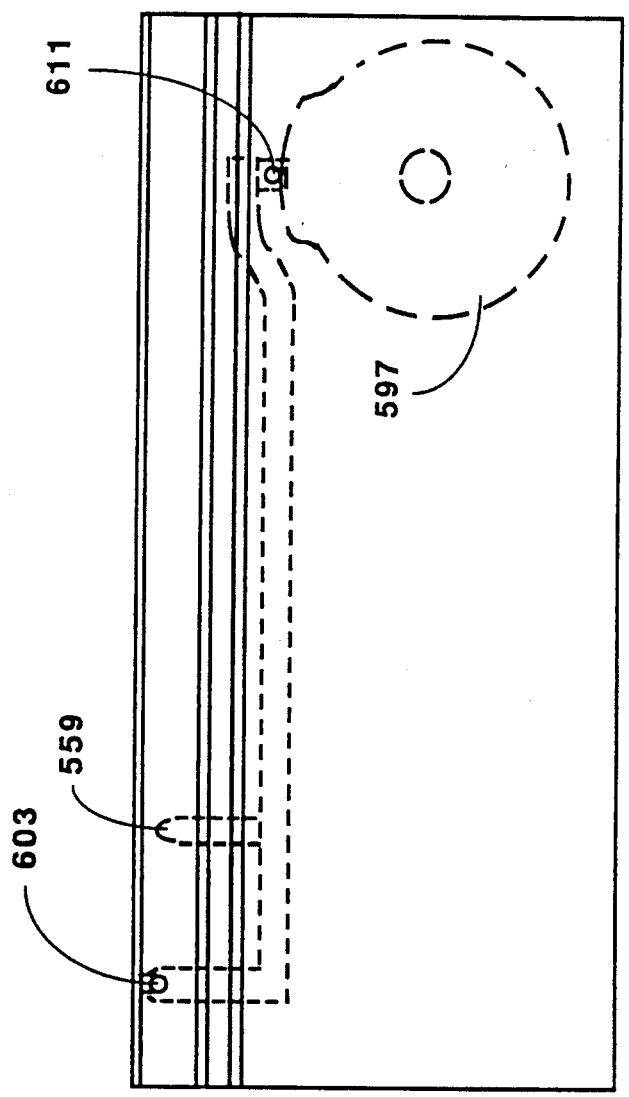
FIG. 26 is a side view of the alternative embodiment in the direction of arrow 613 of FIG. 23.

FIG. 26 is a side view of the controller in the direction of arrow 613 of FIG. 23, to show the position of link 599 and associated elements in the controller.

Figure 27:
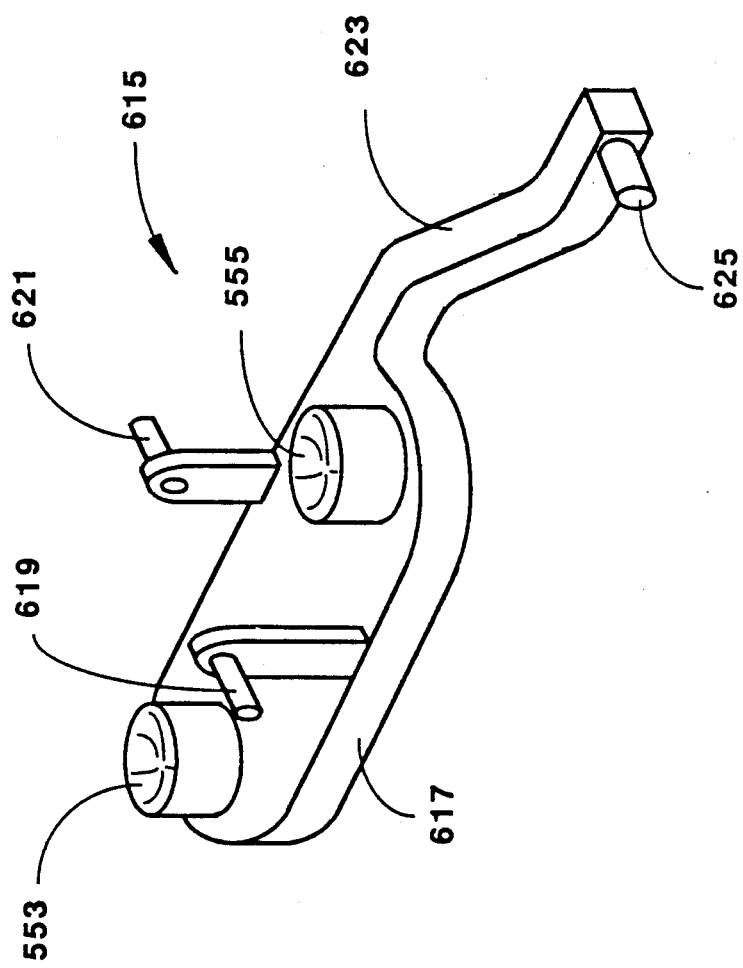
FIG. 27 shows a link for operating actuator rods of the alternative embodiment of FIG. 23.

FIG. 27 shows a link 615 for operating the actuator rods that operate the pumping subchambers. Platform 617 has extensions forming a yoke with two pivot shafts 619 and 621. The platform also carries pumping subchamber actuators 553 and 555. An arm 623 has a cam follower 625 that engages a groove in face-groove portion 595 of combination cam 591. As the cam rotates, the rocking action generated around the pivot shafts causes the actuators to operate exactly opposite one another, so as one pumping subchamber is depressed, the other is allowed to expand.

Figure 28:
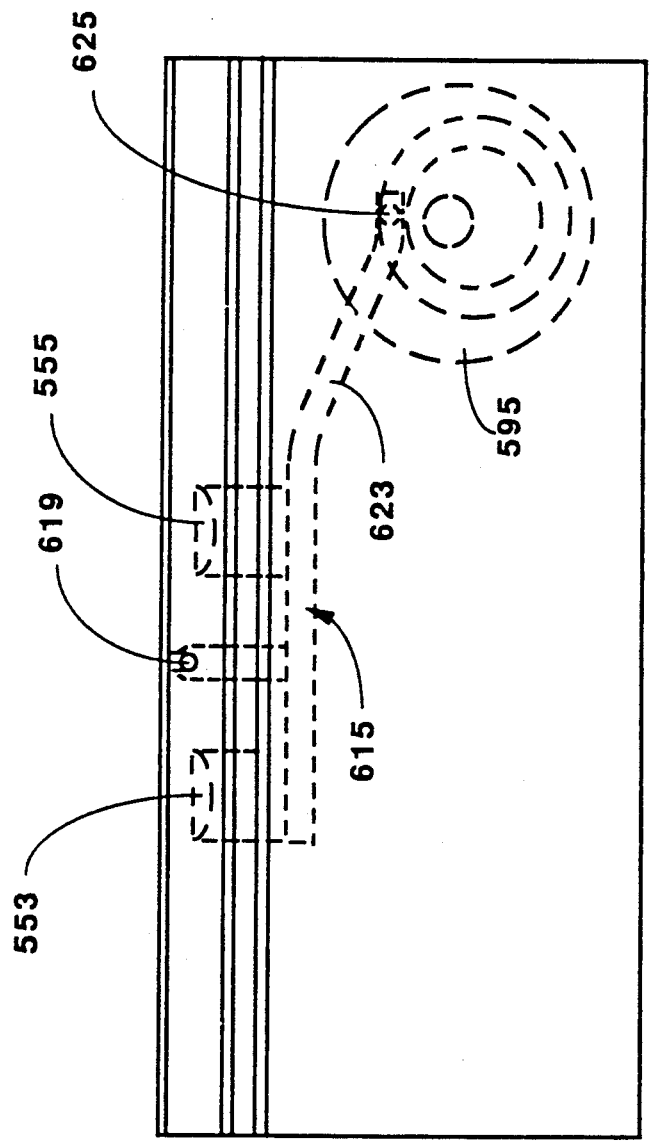
FIG. 28 is a side view of the controller of the alternative embodiment similar to side view FIG. 26, which shows the position of the link illustrated in FIG. 27.

FIG. 28 is a side view of the controller similar to side view FIG. 26, to show the position of link 615 in the controller.

Figure 29:
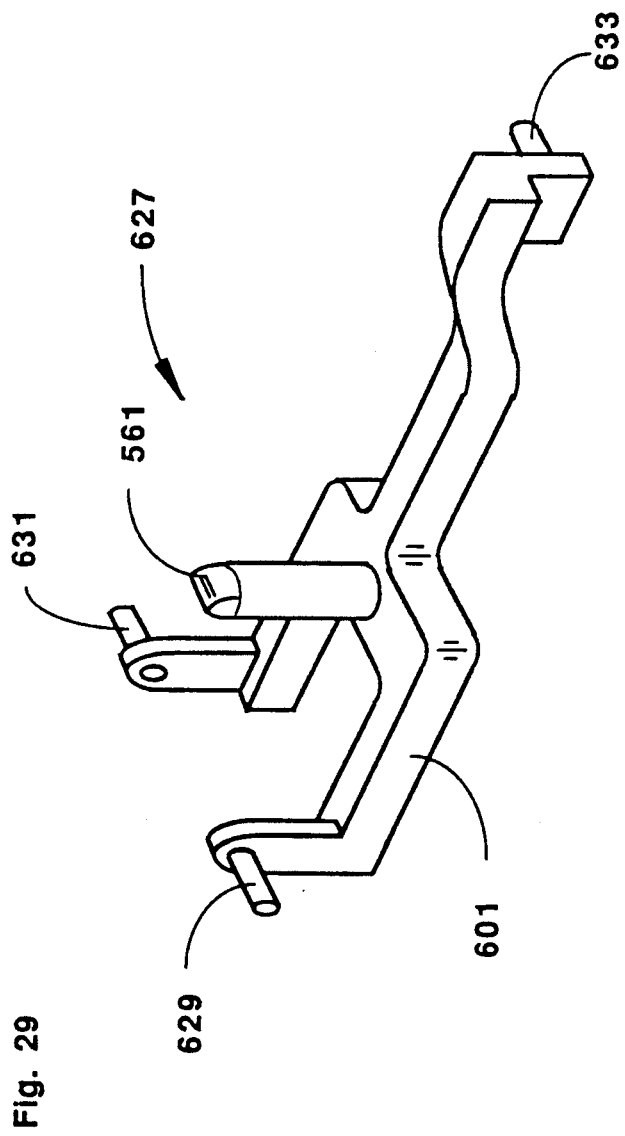
FIG. 29 shows a yet another link for driving a valve actuator in the alternative embodiment of FIG. 23.

FIG. 29 shows a link 627 for driving valve actuator 561 for the transfer valve. This link is similar to link 599 that operates the exit valve. Pivot shafts 629 and 631 engage the body of the controller, and cam follower 633 follows the edge of edge cam portion 593 of combination cam 591.

Figure 30:
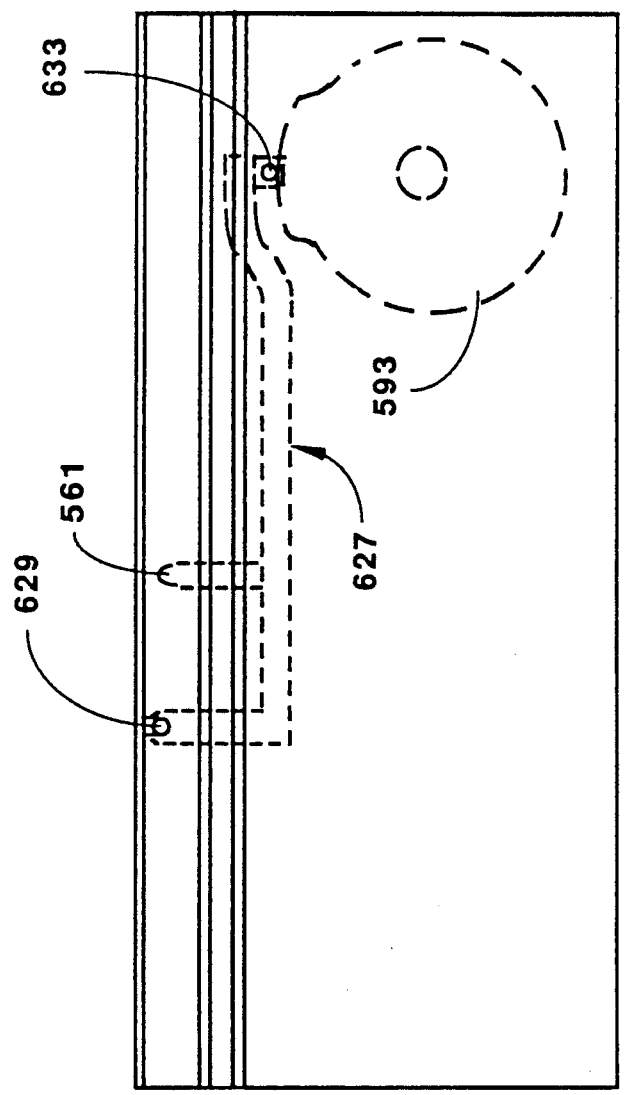
FIG. 30 is a side view similar to FIGS. 26 and 28 to show the position of the link of FIG. 29.

FIG. 30 is a side view similar to FIGS. 26 and 28 to show the position of link 627 in the controller.

The three links for operating the actuators of the controller are machined from nylon plastic material in the preferred embodiment, although there are other suitable materials. The shape and position of the various portions of the links are chosen to avoid interference between the links over the range of movement required for operation.

The controller shown by FIG. 23 is designed to be operable as a positive pump flow controller and also as a drip rate device using the algorithm previously described, just as the other preferred embodiments. With the motor running in the direction to rotate idler shaft 583 in the direction shown by arrow 637, the controller operates as a positive flow controller, opening and closing the transfer and exit valves and operating the pumping subchamber substantially in the sequence shown by FIGS. 9(A) through 9(G). To operate as a drip rate controller, it is necessary that the exit valve be settable at any position between its full open and full closed position, while the transfer valve is fully open.

Figure 31:
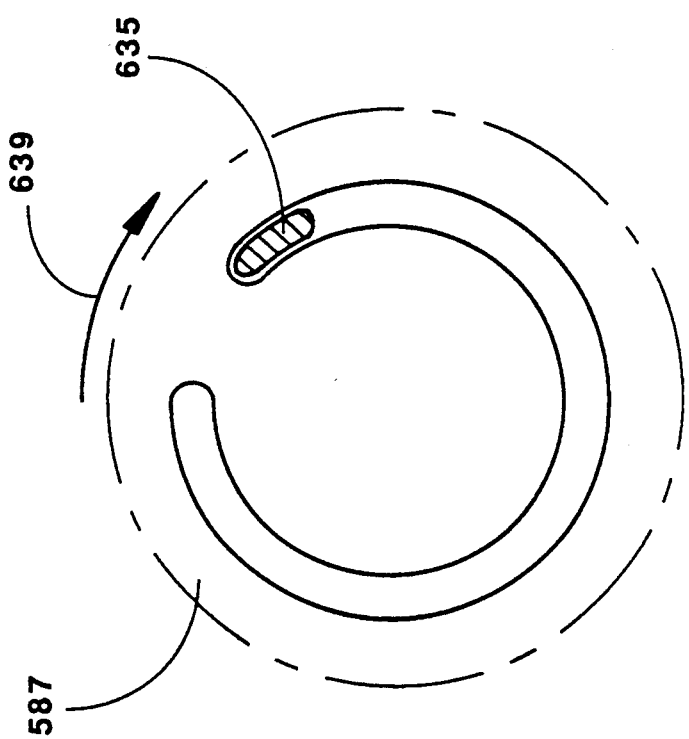
FIG. 31 shows a face of a gear in the direction of section line A of FIG. 24.

Combination cam 591 is not fixed to camshaft 589, but is mounted on the camshaft through a clearance hole, and rotatable relative to the camshaft. Gear 587 has a circular groove on the face toward cam 591, and a projection 635 from cam 591 engages the circular groove. FIG. 31 shows the face of gear 587 in the direction of section line and arrow A of FIG. 24. In this view, since FIG. 24 is a bottom view, the vertical orientation is reversed. The direction of rotation for operation as a positive flow controller is accordingly clockwise as shown by arrow 639. The circular groove in gear 587 is groove 641. As gear 587 rotates, projection 635 is encountered and combination cam 591 is rotated along with the gear. If the motor is stopped and reversed, combination cam 591 will not be driven unless the gear rotates counterclockwise the full angular extent of the groove, which is about 300 degrees. To operate as a drip rate controller, the motor is stopped with valve actuator 561 fully open, and the position of actuator 559 is set by driving the motor in reverse. The full range of closure of the exit valve by position of valve actuator 559 may be realized within the 300 degree allowance of the groove.

FIG. 25 shows two cam followers for link 599 that operates valve actuator 559 that controls the exit valve, follower 609, and follower 611. Follower 611, as described above, follows cam 597 to control the exit valve in operation as a positive flow controller. By driving the motor in reverse, cam 643 controls the position of actuator 559 for the exit valve through follower 609.

Figure 32:
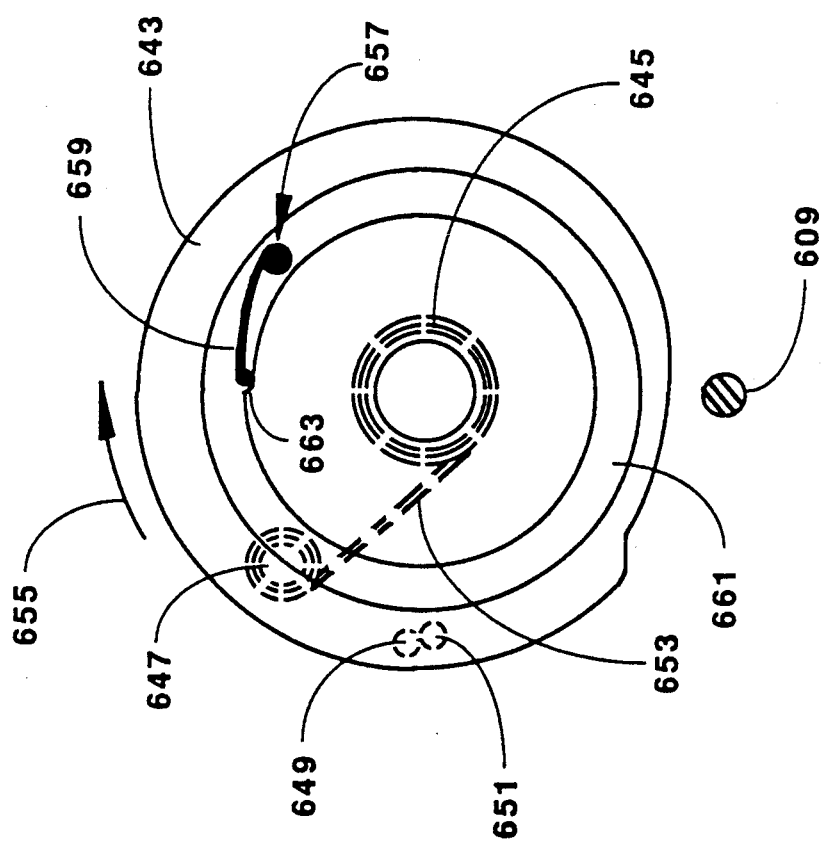
FIG. 32 shows a spring arrangement for the gear train of the controller of FIG. 23. The spring arrangement is shown in phantom view from the section line B in the direction of the arrow.

Cam 643 is mounted to rotate on cam shaft 589 similar to cam 591, but is urged to rotate clockwise (viewed in the same orientation as FIG. 31) by a spring arrangement. The spring arrangement is shown in FIG. 32 in phantom view from the section line B in the direction of the arrow. A tempered leaf spring material 563, about 0.2 mm in thickness, is wound on hub 647, which is fixed to the controller frame. This material is extended from hub 647 to hub 645, which is a part of cam 643, and the spring material is wound around hub 645 and secured to hub 645, so that a constant torque is applied to cam 643 to urge the cam to rotate clockwise in the direction of arrow 655. This torque is provided by virtue of the spring material trying to rewind on hub 647. Cam 643 has a stop pin 651 which bears against a stop pin 649 that is fixed to the controller body. Cam 643 is held in the position with the two stop pins in contact, not rotating, while the controller operates as a positive flow controller.

Gear 587 has a spring-pawl 657 attached which engages a groove 661 in cam 643. The groove is substantially circular except for a small step 663. The spring-pawl has a leaf spring extension 659 positioned so that the free end (adjacent step 663) urges against the inside (toward the center of curvature) of the groove. As gear 587 rotates clockwise carrying the spring-pawl clockwise in FIG. 32, cam 643 does not move, because the friction of the spring-pawl in the groove is not enough to move the cam against the influence of the coiled spring.

To operate the controller as a drip controller, the motor is stopped in a "home" position with the transfer valve fully open and the exit valve fully closed. The motor is then reversed, and gear 587 begins to rotate carrying spring-pawl 657 counterclockwise in FIG. 32. When the end of extension 659 encouters step 663 enough torque is transferred to cam 643 to rotate the cam counterclockwise against the coil spring. As the major diameter of cam 643 engages follower 609, cam 597 (not shown) retreats from the follower and allows cam 643 complete control. As rotation continues, valve actuator 659 gradually opens the exit valve. The full extent of travel of the valve actuator is represented in about 270 degrees of rotation of cam 643, so reverse rotation of the motor may be discontinued at any point to match drip rate with previously recorded volume flow data. As a safety measure, if reverse rotation is continued beyond the range of the valve actuator, stop pin 651 will encounter spring coil 647 stopping cam 643. Gear 587 will continue to rotate and the spring-pawl will ride up and over step 663. Cam 643 will then rotate clockwise until the stop pins engage. Further ratation of the gear in the same direction will re-engage the spring-pawl with the step, and the action will repeat. No damage is done to the mechanism.

What is claimed is:

1. A pumping chamber for use with a pump actuator for infusing fluids into patients comprising:

base means for providing a base surface defining one side of the pumping chamber;

a top portion having an inner surface spaced-apart from said base surface of said base means and an outer surface for contacting the pump actuator which is used for moving said top portion relative to said base means, said top portion for providing the other side of the pumping chamber;

flexible wall means connected to the base surface of the base means and to the inner surface of the top portion for providing a volume therebetween, said flexible wall means having a first perimeter where it attaches to the top portion and a second perimeter where it attaches to the base means, said flexible wall means constructed of a material having a modulus of elasticity and a thickness such that when said pump actuator is not moving, said flexible wall means does not collapse when subjected to a negative gauge pressure, said elasticity and said thickness also such that said flexible wall means bends when the pump actuator moves the top portion relative to the base means;

inlet/outlet means for providing an inlet opening to permit an infusate into said volume and an outlet opening for permitting said infusate out of said volume; wherein, said stiff non-compliant surface of said base means and said inner surface of said cap means are substantially planar and oriented parallel to each other; and wherein, an orthogonal projection of the second perimeter onto the plane of the inner surface of said cap means contains the first perimeter; and wherein said wall means has a thickness in a cross-section orthogonal to the first plane which is the same at the first perimeter as it is at the second perimeter.

2. A disposable pumping apparatus for use with first and second actuators for infusing fluids into patients under a pumping pressure, comprising:

base means for providing a base surface;

a first top portion having an inner surface spaced apart from said base surface and an outer surface positioned to contact said first actuator, said first top portion providing one side of said first pumping subchamber, an other side of said first pumping subchamber being provided by the base surface;

first flexible wall means connected to the base surface and to the inner surface of the first top portion for providing a first volume therebetween defining said first pumping subchamber, said first flexible wall means constructed of a material having a modulus of elasticity and a thickness such that when said first actuator is not moving said first cap means, said first flexible wall means does not collapse when subjected to a negative gauge pressure, said elasticity and said thickness also such that said first flexible wall means bends when said first actuator moves the first top portion relative to the base means;

a second top portion having an inner surface spaced apart from said base surface and an outer surface positioned to contact said second actuator, said second top portion for providing one side of said second pumping subchamber, an other side of said second pumping subchamber being provided by the base surface; and second flexible wall means connected to the base surface and to the inner surface of the second top portion for providing a second volume therebetween defining said second pumping subchamber, said second flexible wall means constructed of a material having a modulus of elasticity and a thickness such that when said second actuator is not moving said second top portion, said second flexible wall means does not collapse when subjected to said negative gauge pressure, said elasticity and said thickness also such that said second flexible wall means bends when said second actuator means moves the second top portion relative to the base means;

inlet means connected to the first volume for permitting fluids to enter the first volume;

transfer means connected to the first volume and the second volume for providing a conduit for fluids being transferred between the first volume and the second volume;

outlet means connected to the second volume for permitting fluids to exit the second volume and wherein said outer surface of said first top portion is domed outwards relative to said base surface.

3. A disposable pumping apparatus as in claim 2 wherein said first top portion is constructed of the same material as said first flexible wall means and wherein said first top portion has a thickness greater than the thickness of said first flexible wall means.

4. An infusion system comprising:
a disposable flow chamber having first and second pumping subchambers connected by a first collapsible passageway, said flow chamber having an inlet passageway connected to said first subchamber, and said flow chamber having an outlet collapsible passageway connected to said second subchamber permitting infusate to exit from said second subchamber;

pump drive means having a first actuator means for changing the volume of said first subchamber and a second actuator means for changing the volume of said second subchamber, said pump drive means having first control valve means for depressing said first collapsible passageway to control flow of infusate between said first subchamber and said second subchamber, and having an outlet control valve means for depressing said outlet collapsible passageway to control flow of infusate leaving said second subchamber, said pump drive means having a motor means for driving said first and second actuator means, said first control valve means and said outlet control valve means, to pump infusate through said flow chamber, said pump drive means also having means for moving said outlet control valve means with said motor means while said first control valve means is held fixed.

5. An infusion system as in claim 4 further comprising control means for controlling said motor means to cause pumping of infusate through said disposable flow chamber followed by a calibrated passive flow of infusate through said disposable flow chamber.

6. An infusion system as in claim 4 wherein said motor means comprises a single motor.

7. An infusion system comprising:
a disposable flow chamber having first and second pumping subchambers connected by a first collapsible passageway, said flow chamber having an inlet passageway connected to said first subchamber, and said flow chamber having an outlet collapsible passageway connected to said second subchamber permitting infusate to exit from said second subchamber;

pump drive means having a first actuator means for changing the volume of said first subchamber and a second actuator means for changing the volume of said second subchamber, said pump drive means having first control valve means for depressing said first collapsible passageway to control flow of infusate between said first subchamber and said second subchamber, and having an outlet control valve means for depressing said outlet collapsible passageway to control flow of infusate leaving said second subchamber, said pump drive means having a motor means for driving said first and second actuator means, said first control valve means and said outlet control valve means, to pump infusate through said flow chamber; and pump drive means also having means for moving said outlet control valve means with said motor means while said first control valve means is held fixed beam means coupled to said first and second actuator means for causing equal and opposite volume changes during pumping for said first and second subchambers.

8. An infusion system as in claim 7, wherein said first and second subchambers have equal maximum volumes.

9. An infusion system as in claim 7, wherein said beam means is pivoted.

10. An infusion system comprising:
a disposable flow chamber having first and second pumping subchambers connected by a first collapsible passageway, said flow chamber having an inlet passageway connected to said first subchamber, and said flow chamber having an outlet collapsible passageway connected to said second subchamber permitting infusate to exit from said second subchamber;

pump drive means having a first actuator means for changing the volume of said first subchamber and a second actuator means for changing the volume of said second subchamber, said pump drive means having first control valve means for depressing said first collapsible passageway to control flow of infusate between said first subchamber and said second subchamber, and having an outlet control valve means for depressing said outlet collapsible passageway to control flow of infusate leaving said second subchamber, said pump drive means having a motor means for driving said first and second actuator means, said first control valve means and said outlet control valve means, to pump infusate through said flow chamber; pump drive means also having means for moving said outlet control valve means with said motor means while said first control valve means is held fixed; and said disposable flow chamber comprising:
base means for providing a base surface;

a first top portion having an inner surface spaced apart from said base surface and an outer domed surface positioned to contact said first actuator means, said first top portion for providing one side of said first pumping subchamber, an other side of said first pumping subchamber being provided by the base surface;

first flexible wall means connected to the base surface and to the inner surface of the first top portion for providing a first volume therebetween defining said first pumping subchamber;

said first flexible wall means and said first top portion constructed of materials having a modulus of elasticity and a thickness such that when said first actuator means is not moving said first top portion, said first flexible wall means and said first top portion do not collapse when subjected to a negative gauge pressure, said elasticity and said thickness also such that said first flexible wall means when said first actuator means moves the first top portion relative to the base means;

second top portion having an inner surface spaced apart from said base surface and an outer domed surface positioned to contact said second actuator means, said second top portion for providing one side of said second pumping subchamber, an other side of said second pumping subchamber being provided by the base surface; and second flexible wall means connected to the base surface and to the inner surface of the second top portion for providing a second volume therebetween defining said second pumping subchamber;

said second flexible wall means and said second top portion constructed of materials having a modulus of elasticity and a thickness such that when said second actuator means is not moving said second top portion, said second flexible wall means and said second top portion do not collapse when subjected to said negative guage pressure, said elasticity and said thickness also such that said second flexible wall means bend when said second actuator means moves the second top portion relative to the base means.

11. An infusion system as in claim 10 wherein said negative gauge pressure is at least 15 torr.

12. An infusion system as in claim 10 wherein said negative gauge pressure is at least 30 torr.

13. An infusion system as in claim 10 wherein said negative gauge pressure is at least 100 torr.

14. A disposable pumping apparatus configured for being held by a drive system having first and second actuators for infusing fluids into patients under a pumping pressure, comprising:

base means for providing an inner base surface and having an outer base surface for contacting said drive system;

a first top portion having an inner surface spaced apart from said inner base surface and an outer domed surface configured to contact said first actuator without being attached thereto when said apparatus is held by said drive system, said first top portion for providing one side of said first pumping subchamber, an other side of said first pumping subchamber being provided by the base surface;

first flexible wall means connected to the inner base surface and to the inner surface of the first top portion for providing a first volume therebetween defining said first pumping subchamber;

said first flexible wall means and said first top portion constructed of materials having a modulus of elasticity and a thickness such that when said first actuator is not moving said first top portion, said first flexible wall means and said first top portion do not collapse when subjected to a negative guage pressure, said elasticity and said thickness also such that said first flexible wall means bends when said first actuator moves the first top portion relative to the base means;

second top portion having an inner surface spaced apart from said inner base surface and an outer surface configured to contact said second actuator without being attached thereto when said apparatus is held by said drive system, said second top portion for providing one side of said second pumping subchamber, an other side of said second pumping subchamber being provided by the base surface; and second flexible wall means connected to the inner base surface and to the inner surface of the second top portion for providing a second volume therebetween defining said second pumping subchamber;

said second flexible wall means and said second top portion constructed of materials having a modulus of elasticity and a thickness such that when said second actuator is not moving said second top portion, said second flexible wall means and said second top portion do not collapse when subjected to said negative gauge pressure, said elasticity and said thickness also such that said second flexible wall means and said second top portion bend when said second actuator means moves the second top portion relative to the base means;

inlet means connected to the first volume for permitting fluids to enter the first volume;

transfer means connected to the first volume and the second volume for providing a conduit for fluids being transferred between the first volume and the second volume;

outlet means connected to the second volume for permitting fluids to exit the second volume.

15. A disposable pumping apparatus as in claim 14 wherein said inner surface of said of base means is a flat rigid surface.

16. A disposable pumping apparatus as in claim 14 wherein said negative gauge pressure is at least 15 torr.

17. A disposable pumping apparatus as in claim 14 wherein said negative gauge pressure is at least 30 torr.

18. A disposable pumping apparatus as in claim 14 wherein said negative gauge pressure is at least 100 torr.

19. An infusion system comprising:

a disposable flow chamber having first and second pumping subchambers connected by a first collapsible passageway, said flow chamber having an inlet passageway connected to said first subchamber, and said flow chamber having an outlet collapsible passageway connected to said second subchamber permitting infusate to exit from said second subchamber;

pump drive means having a first actuator means for changing the volume of said first subchamber and a second actuator means for changing the volume of said second subchamber, said pump drive means having first control valve means for depressing said first collapsible passageway to control flow of infusate between said first subchamber and said second subchamber, and having an outlet control valve means for depressing said outlet collapsible passageway to control flow of infusate leaving said second subchamber, said pump drive means having a motor means for driving said first and second actuator means, said first control valve means and said outlet control valve means, to pump infusate through said flow chamber; pump drive means having for moving said outlet control valve means with said motor means while said first control valve means is held fixed; and said disposable flow chamber comprising:
  base means for providing a base surface;
  a first top portion having an inner surface spaced apart from said base surface and an outer surface positioned to contact said first actuator means, said first top portion providing one side of said first pumping subchamber, an other side of said first pumping subchamber being provided by the base surface;
  first flexible wall means connected to the base surface and to the inner surface of the first top portion, thereby providing a first volume therebetween defining said first pumping subchamber, said first flexible wall means constructed of a material having a modulus of elasticity and a thickness such that when said first actuator means is not moving said first top portion, said first flexible wall means does not collapse when subjected to a negative gauge pressure, said elasticity and said thickness also such that said first flexible wall means bends when said first actuator means moves the first top portion relative to the base means;
  a second top portion having an inner surface spaced apart from said base surface and an outer surface positioned to contact said second actuator means, said second top portion providing one side of said second pumping subchamber, an other side of said second pumping subchamber being provided by the base surface; and
  second flexible wall means connected to the base surface and to the inner surface of the second top portion, thereby providing a second volume therebetween defining said second pumping subchamber, said second flexible wall means constructed of a material having a modulus of elasticity and a thickness such that when said second actuator means is not moving said second top portion, said second flexible wall means does not collapse when subjected to said negative guage pressure, said elasticity and said thickness also such that said second flexible wall means bends when said second actuator means moves the second top portion relative to the base means.

20. An infusion system as in claim 19 wherein said first top portion, said first flexible wall means, said second top portion, said second flexible wall means, a portion of said first collapsible means passageway, a portion of said inlet passageway, and a portion of said outlet collapsible passageway are an integral molded part, all made of the same material, and wherein said molded part is sealed to said base surface to form said first and second volumes, said inlet passageway, said first collapsible passageway, and said outlet collapsible passageway, with one wall of said inlet passageway, one wall of said first collapsible passageway, and one wall of said outlet collapsible passageway being said base surface with the balance of said inlet passageway, said first collapsible passageway, and said outlet collapsible passageway being defined by said molded part.

21. An infusion system as in claim 19 wherein said negative gauge pressure is at least 15 torr.

22. An infusion system as in claim 19 wherein said negative gauge pressure is at least 30 torr.

23. An infusion system as in claim 19 wherein said negative gauge pressure is at least 100 torr.

24. An infusion system as in claim 19, wherein said outer surface of said first top portion is domed outwards relative to said base surface.

25. An infusion system as in claim 24, wherein said first top portion is constructed of the same material as said first flexible wall means and wherein said first top portion has a thickness greater than the thickness of said first flexible wall means.

26. An infusion system as in claim 19, wherein said outer surface of said second top portion is domed outwards relative to said base surface.

27. An infusion system as in claim 26, wherein said second top portion is constructed of the same material as said second flexible wall means and wherein said second top portion has a thickness greater than the thickness of said second flexible wall means.

28. An infusion system as in claim 19, wherein said outer surfaces of said first top portion and said second top portion are domed outwards relative to said base surface.

29. An infusion system as in claim 28, wherein said first top portion is constructed of the same material as said first flexible wall means and wherein said first top portion has a thickness greater than the thickness of said first flexible wall means, and wherein said second top portion is constructed of the same material as said second flexible wall means and wherein said second top portion has a thickness greater than the thickness of said second flexible wall means.

* * * * *